United States Patent [19]
Levine et al.

[11] Patent Number: 6,110,743
[45] Date of Patent: *Aug. 29, 2000

[54] DEVELOPMENT AND USE OF HUMAN PANCREATIC CELL LINES

[75] Inventors: Fred Levine, Del Mar, Calif.; Sijian Wang, Dallas, Tex.; Gillian M. Beattie, Poway; Alberto Hayek, La Jolla, both of Calif.

[73] Assignees: The Regents of the University of California, Oakland; Whittier Institute for Diabetes and Endocrinology, La Jolla, both of Calif.

[ * ] Notice: This patent is subject to a terminal disclaimer.

[21] Appl. No.: 08/883,640

[22] Filed: Jun. 26, 1997

Related U.S. Application Data

[63] Continuation-in-part of application No. 08/509,121, Jul. 31, 1995, Pat. No. 5,723,333, which is a continuation-in-part of application No. 08/386,897, Feb. 10, 1995, abandoned.

[51] Int. Cl.$^7$ ............................... C12N 5/10; C12N 15/63

[52] U.S. Cl. ....................... 435/456; 435/320.1; 435/325; 435/366

[58] Field of Search ............................... 435/172.1, 172.3, 435/320.1, 325, 366, 456

[56] References Cited

U.S. PATENT DOCUMENTS

| | | | |
|---|---|---|---|
| 5,256,553 | 10/1993 | Overell | 435/456 |
| 5,629,159 | 5/1997 | Anderson | 435/6 |
| 5,723,333 | 3/1998 | Levine et al. | 435/325 |

FOREIGN PATENT DOCUMENTS

| | | |
|---|---|---|
| 91/09939 | 7/1991 | WIPO . |
| 91/12329 | 8/1991 | WIPO . |
| 95/29989 | 11/1995 | WIPO . |

OTHER PUBLICATIONS

Yarranton (1992) Inducible vectors for expression in mammalian cells. Curr. Opin. Biotechnol. 3:506–511, Oct. 1992.

Baekkeskov, S. et al., "Autoantibodies in newly diagnosed diabetic children immunoprecipitate human pancreatic islet cell proteins" *Nature* 298:167–169 (1982).

Bartek, J. et al., "Efficient immortalization of luminal epithelial cells from human mammary gland by introduction of simian virus 40 large tumor antigen with a recombinant retrovirus" *Proc. Natl. Acad. Sci. USA* 88:3520–3524 (1991).

Beattie, G.M., et al., "Acid β-Galactosidase: A Developmentally Regulated Marker of Endocrine Cell Precursors in the Human Fetal Pancreas" *J. Clin. Endocr. Metab.* 78:1232 (1994).

Burns, J.C. et al., "Vesicular stomatitis virus G glycoprotein pseudotyped retroviral vectors: Concentration to very high titer and efficient gene transfer into mammalian and non-mammalian cells" *Proc. Natl. Acad. Sci. USA* 90:8033–8037 (1993).

Chou, J.Y., "Differentiated Mammalian Cell Lines Immortalized by Temperature–Sensitive Tumor Viruses" *Mol. Endocrinol.* 3(10):1511–1514 (1989).

Clark, S.A. et al., "Modulation of Glucose–Induced Insulin Secretion from a Rat Clonal β–Cell Line" *Endocrinol.* 127(6):2779–2788 (1990).

Dale, E.C. and Ow, D.W., "Gene transfer with subsequent removal of the selection gene from the host genome" *Proc. Natl. Acad. Sci. USA* 88:10558–10562 (1991).

Efrat, S. et al., "β–cell lines derived from transgenic mice expressing a hybrid insulin gene–oncogene" *Proc. Natl. Acad. Sci. USA* 85:9037–9041 (1988).

Efrat, S. et al., "Conditional transformation of a pancreatic β–cell line derived from transgenic mice expressing a tetracycline–regulated oncogene" *Proc. Natl. Acad. Sci. USA* 92:3576–3580 (1995).

Efrat, S. et al., "Development of Correctly Regulated Pancreatic B–cell Lines" *J. Cellular Biochem. Suppl.* 21B:4 (1995).

Eilers, M. et al., "Chimaeras of Myc oncoprotein and steroid receptors cause hormone–dependent transformation of cells" *Nature* 340:66–68 (1989).

Epstein–Baak, R. et al., "Inducible Transformation of Cells from Transgenic Mice Expressing SV40 under lac Operon Control" *Cell Growth Diff.* 3:127–134 (1992).

Figge, J. et al., "Stringent Regulation of Stably Integrated Chloramphenicol Acetyl Transferase Genes by E. coli lac Repressor in Monkey Cells" *Cell* 52:713–722 (1988).

Gilligan, A. et al., "Functional Pancreatic β–Cell Line From SV40 T–Antigen Transgenic Mouse" *Diabetes* 38:1056–1062 (1989).

Gueli, N. et al., "In vitro growth of a cell line originated from a human insulinoma" *Exp. Clin. Cancer Res.* 6(4):281–285 (1987).

Hughes, S.D. et al., "Engineering of glucose–stimulated insulin secretion and biosynthesis in non–islet cells" *Proc. Natl. Acad. Sci. USA* 89:688–692 (1992).

Jang, S.K. et al., "A Segment of the 5' Nontranslated Region of Encephalomyocarditis Virus RNA Directs Internal Entry of Ribosomes during In Vitro Translation" *J. Virol.* 62(8):2636–2643 (1988).

(List continued on next page.)

*Primary Examiner*—Robert A. Schwartzman
*Attorney, Agent, or Firm*—Townsend & Townsend & Crew LLP

[57] ABSTRACT

This invention relates to cell lines, particularly mammalian cell lines, established by transforming the cells with vectors, preferably retroviral vectors, containing two or more oncogenes under the control of one or more inducible promoters and/or genetic elements. Also within the scope of the invention are human cell lines with extended in vitro lifespan, transformed by vectors containing one or more oncogenes under the control of one or more, preferably exogenous, inducible promoters and/or genetic elements. The vectors may additionally contain gene(s) encoding for desired gene product(s). Also disclosed are insulin producing human pancreatic cell lines useful for transplantation into human diabetic patients.

27 Claims, 8 Drawing Sheets

OTHER PUBLICATIONS

Jehn, B. et al., "Overexpression of Mos, Ras, Src, and Fos Inhibits Mouse Mammary Epithelial Cell Differentiation" *Mol. Cell Biol.* 12(9):3890–3902 (1992).

Knaack, D. et al., "Clonal Insulinoma Cell Line That Stably Maintains Correct Glucose Responsiveness" *Diabetes* 43:1413–1417 (1994).

Larsen, J. et al., "The v–ski oncogene cooperates with the v–sea oncogene in erythoid transformation by blocking erythoid differentiation" *Oncogene* 7:1903–1911 (1992).

Levine, F. et al., "Development of a Cell Line From the Human Fetal Pancreas" *Transplantation Proc.* 27(6):3410 (1995).

Levine, F. et al., "Efficient gene expression in mammalian cells from a dicistronic transcriptional unit in an improved retroviral vector" *Gene* 108:167–174 (1991).

Liloglou et al., "Inducible H–ras gene expression controlled by an allosterically regulated transactivator" *Oncology Reports* 1:889–893 (1994).

Liu et al., "Control of Ha–ras–medicated mammalian cell transformation by *Escherichia coli* regulatory elements" *Cancer Res.* 52:983–989 (1992).

Maniatis et al., in: Molecular Cloning: A Laboratory Manual, Cold Spring Harbor Laboratory Press, 2nd Edition (1989).

Miyazaki, J.–I. et al., "Establishment of a Pancreatic β Cell Line That Retains Glucose–Inducible Insulin Secretion: Special Reference to Expression of Glucose Transporter Isoforms" *Endocrinol.* 127(1):126 (1990).

Newgard, C.B., "Cellular Engineering and Gene Therapy Strategies for Insulin Replacement in Diabetes" *Diabetes* 43:341–350 (1994).

Pääbo, S. et al., "A Short Sequence in the COOH–Terminus Makes an Adenovirus Membrane Glycoprotein a Resident of the Endoplasmic Reticulum" *Cell* 50:311–317 (1987).

Parks, G.D. et al., "Encephalomyocarditis Virus 3C Protease: Efficient Cell–Free Expression from Clones Which Link Viral 5' Noncoding Sequences to the P3 Region" *J. Virol.* 60(2):376–384 (1986).

Quaife, C.J. et al., "Pancreatic Neoplasia Induced by ras Expression in Acinar Cells of Transgenic Mice" *Cell* 48:1023–1034 (1987).

Radvanyi, F. et al., "Pancreatic β Cells Cultured from Individualized Preneoplastic Foci in a Multistage Tumorigenesis Pathway: A Potentially General Technique for Isolating Physiologically Representative Cell Lines" *Mol. Cell. Biol.* 13(7):4223–4232 (1993).

Rosen, C.A. et al., "Construction of Recombinant Murine Retroviruses That Express the Human T–Cell Leukemia Virus Type II and Human T–Cell Lymphotropic Virus Type III trans Activator Genes" *J. Virol.* 57(1):379–384 (1986).

Sandgren, E.P. et al., "Pancreatic tumor pathogenesis reflects the causative genetic lesion" *Proc. Natl. Acad. Sci. USA* 88:93–97 (1991).

Shay, J.W. et al., "Quantification of the Frequency of Immortalization of Normal Human Diploid Fibroblasts by SV40 Large T–Antigen" *Exp. Cell Res.* 184:109–118 (1989).

Soldevila, G. et al., "Transfection with SV40 Gene of Human Pancreatic Endocrine Cells" *J. Autoimmunity* 4:381–396 (1991).

Wang, S. et al., "Analysis of a Human Fetal Pancreatic Islet Cell Line" *Transplantation Proc.* 29:2219 (1997).

Wang, S. et al., "Analysis of a Human Fetal Pancreatic Islet Cell Line" *Proc. Am. Assoc. Cancer Res. Annual Meeting* 36:182 Abstract No. 1086 (1995).

Wang, S. et al., "Development of a VSV–G protein pseudotyped retroviral vector system expressing dominant oncogenes from a lacO–modified inducible LTR promoter" *Gene* 182:145–150 (1996).

Wang, S. et al., "Isolation and Characterization of a Cell Line from the Epithelial Cells of the Human Fetal Pancreas" *Cell Transplantation* 6(1):59–67 (1997).

Westerman, K.A. et al., "Reversible immortalization of mammalian cells mediated by retroviral transfer and site–specific recombination" *Proc. Natl. Acad. Sci. USA* 93:8971–8976 (1996).

Wold, W.S.M. and Gooding, L.R., "Adenovirus Region E3 Proteins that Prevent Cytolysis by Cytotoxic T Cells and Tumor Necrosis Factor" *Mol. Biol. Med.* 6:433–452 (1989).

Wolff, J.A., ed., in: Gene Therapeutics, Methods and Applications of Direct Gene Transfer, Birkhauser, Boston, USA (1994).

Yarranton, G.T., "Inducible vectors for expression in mammalian cells" *Curr. Opinion Biotechnol.* 3:506–511 (1992).

Yee, J.–K. et al., "A general method for the generation of high–titer, pantropic retroviral vectors: Highly efficient infection of primary hepatocytes" *Proc. Natl. Acad. Sci. USA* 91:9564–9568 (1994).

FIG. 4
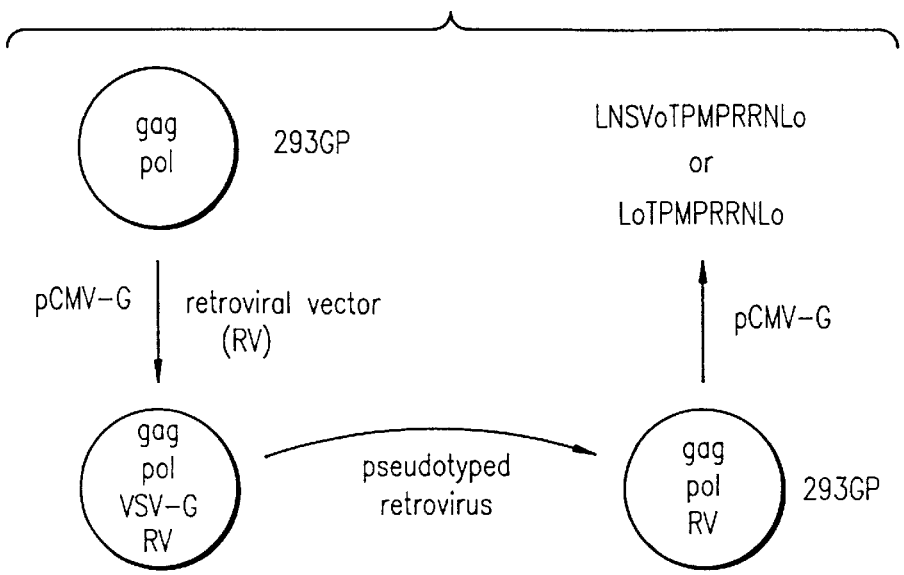
FIG. 5
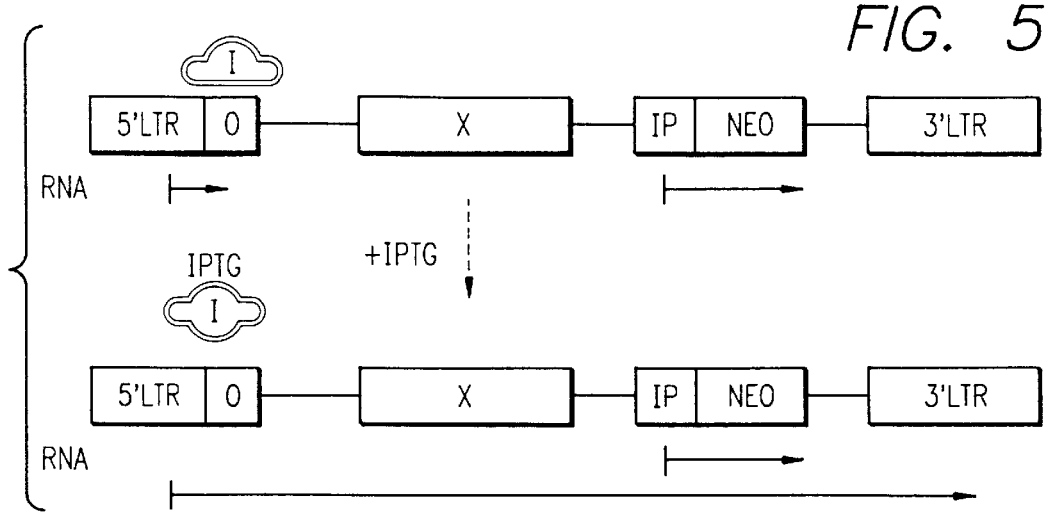
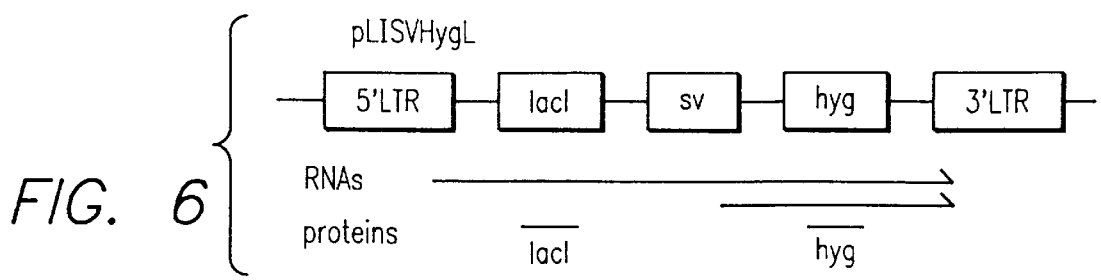
FIG. 6

DEVELOPMENT AND USE OF HUMAN PANCREATIC CELL LINES

This is a continuation-in-part patent application of U.S. patent application Ser. No. 08/509,121 filed on Jul. 31, 1995, U.S. Pat. No. 5,723,333, which was a continuation-in-part patent application of U.S. patent application Ser. No. 08/386,897 filed on Feb. 10, 1995, abandoned, both of which are incorporated by reference in their entirety.

This invention was made with Government support under Grant No. 1R01DK50171-01, awarded by the National Institutes of Health. The Government has certain rights in this invention.

BACKGROUND OF THE INVENTION

This invention relates to genetically engineered cell lines and cell transplantation therapy. In particular, it relates to oncogene-transformed cell lines useful for transplantation.

Insulin is synthesized, processed and secreted by pancreatic β cells, the major endocrine cell type in the islets of Langerhans that are distributed throughout the pancreas. Pancreatic β cells secrete insulin in response to an increase in extracellular glucose concentration.

The two major forms of diabetes, insulin-dependent diabetes mellitus (IDDM) and non-insulin-dependent diabetes mellitus (NIDDM) both are characterized by an inability to deliver insulin in an amount and with the precise timing that is needed for control of glucose homeostasis. The inadequate insulin delivery is caused by: β-cell destruction by autoimmune mechanisms in IDDM, and β-cell dysfunction closely coupled to insulin resistance in NIDDM. Despite these differences in etiology, a common therapeutic goal for the two disorders is to restore the capacity for glucose-mediated insulin release to its normal level.

Treatment of IDDM requires insulin replacement, either by conventional administration of the hormone or by transplantation of insulin-secreting tissue. Since the latter strategy has thus far relied largely on the use of scarce human pancreas as the insulin source, it has not been feasible for general application. Some investigators have proposed the use of xenografts, e.g., porcine, as a means of overcoming the problem of tissue availability. However, the immune barrier to xenografts is formidable, even using techniques such as encapsulation to help them evade the host immune response.

A number of investigators have developed pancreatic β-cell lines using transgenic mice expressing dominant oncogenes, particularly SV40 T-antigen, under control of the insulin promoter {Newgard, C. B., Diabetes, 43:341–350 (1994) and Hanahan, D., Nature, 315:33–40 (1985)}. Mice expressing T-antigen under the control of the rat insulin gene promoter develop β-cell tumors at 12–20 weeks after birth. Unfortunately, most {see Knaack, et al., Diabetes, 43:1413–1417, (1994)} β-cell lines derived from these animals do not retain normal glucose-responsive insulin production {Tal, M., et al., Mol. Cell. Biol., 12:422–32 (1992)}.

In the absence of spontaneously arising cell lines with the desired properties, cell lines can be created by transfer of dominant oncogenes into primary cells {Chou, J. Y., Mol. Endocrinol., 3:1511–14 (1989)}. Such cell lines have been constructed from brain, liver and bone marrow. In some cases, cell lines created in this way retain differentiated functions or the ability to differentiate in vivo {Snyder, E. Y., et al., Cell, 68:33–51 (1992)}. Unfortunately, in many other cases, loss of differentiated function occurs, decreasing the usefulness of the cell line {Jehn, B., et al., Mol. Cell. Biol., 12:3890–3902 (1992)}.

SV40 T-antigen transforms cells by multiple mechanisms including binding and inactivation of the tumor suppressor proteins p53 and retinoblastoma (Rb) {Andersson, A., et al., Transplantation Reviews, 6:20–38 (1992)}. Although SV40 T-antigen has been shown to be sufficient for transformation of rodent cells, human primary cells are more refractory to transformation {Chang, S. E., Biochem. Biophys. Acta, 823:161–94 (1986)}. The frequency of immortalization of human primary fibroblasts transfected with SV40 T-antigen has been estimated to be $3 \times 10^{-7}$ per passage in culture {Shay, J. W., et al., Exp. Cell Res., 184:109–18 (1989)}.

Overexpression of the epidermal growth factor (EGF) receptor is often found in pancreatic cancers, as is overexpression of the EGF homologues c-erbB2 and c-rbB3 {Hall, P. A., et al., Cancer Surveys, 16:135–55 (1993)}. Ras genes are among the ost commonly mutated in human cancer, including pancreatic cancer. Of the ras genes, K-ras mutations are present in 80–90% of pancreatic ductal carcinomas {Hruban, R. H., et al., Am. J. Pathol., 143:545–54 (1993)}. Interestingly, H-ras mutations have not been found in pancreatic cancer {Hruban, R. H., et al., Am. J. Pathol., 143:545–54 (1993) and Smit V. T. H. B. M., et al., Nucl. Acid Res., 16:7773–82 (1988)}. H-ras containing an activating mutation, under the control of the elastase promoter, has been expressed in the exocrine tissue of transgenic mice, with consequent tumor formation {Sandgren, E. P., et al., Proc. Natl. Acad. Sci. USA, 88:93–97 (1991) and Quaife, C. J., et al., Cell, 48:1023–34 (1987)}. However, when activated H-ras was expressed specifically in β-cells using the insulin promoter, destruction of islet cells with diabetes occurred in male mice, but not in females {Efrat, S., et al., Mol. Cell. Biol., 10:1779–83 (1990) and Efrat S., Endocrinol., 128:897–901 (1991)}.

As in many other cancers, p53 is commonly mutated in pancreatic cancers. Although c-myc overexpression has not been studied extensively in primary human tumors, it is a potent transforming gene when expressed in the pancreas of transgenic mice.

Gene Transfer Into Primary Cells

A problem with the development of immortalized cell lines from primary cells, and particularly human primary cells, is that these cells are resistant to most methods of gene transfer. Gene transfer into islet cells has been accomplished by electroporation {German, M. S., et al., J. Biol. Chem., 265:22063–22066 (1990)}. However, gene expression was only studied on a transient basis and required dissociating the islets into a single cell suspension. Such treatment is deleterious to the survival of cells from the human pancreas {Beattie, G., et al., J. Clin. Endocr. Metab., 78:1232–40 (1994)}. Adenovirus vectors efficiently infect pancreatic cells {Newgard, C. B., Diabetes, 43:341–50 (1994)}, but maintaining long term gene expression from these vectors has been a problem {Smith, T. A. G., et al., Nature Genet., 5:397–402 (1993)}. Alternatively, transgenic technology may be used. This usually involves expressing an oncogene, usually SV40 T-antigen, under control of the insulin promoter in transgenic animals, thereby generating cell tumors that can be used for propagating insulinoma cell lines {Efrat, S., et al., Proc. Natl. Acad. Sci. USA, 85:9037–41 (1988); Miyazaki, J. I., et al., Endocrinology, 127:127–32 (1990)}. Cell lines derived by transgenic expression of T-antigen in β-cells exhibit variable phenotypes. Some have little glucose-stimulated insulin release or exhibit maximal responses at subphysiological glucose concentrations, while others respond to glucose concentrations over the physiological range. However, the near normal responsiveness of the latter cell lines is not permanent, as continuous cell culture results in a shift in glucose dose response such that the cells secrete insulin at subphysiological glucose concentrations. A detailed discussion of these cell lines is found in Newgard, C. B., Diabetes, 43:341–350 (1994). A human insulinoma cell line has been obtained but it is difficult to maintain in culture and does not produce insulin {Gueli, N., et al., Exp. Clin. Cancer Res., 6(4):281–285 (1987)}.

Retroviral-mediated gene transfer (i.e., the use of retroviruses to deliver genes into cells) is an alternative gene transfer technology which has met with limited success. In this technique, a desired gene is inserted into a retroviral vector to obtain a recombinant virus which is then used to infect target cells. Retroviruses are ribonucleic acid (RNA) viruses. In retroviral-mediated gene transfer, the viral RNA is first converted to deoxyribonucleic acid (DNA) after an RNA virus penetrates a target cell. If the target cell penetrated is a replicating cell (i.e., mitotically active), the DNA will enter the nucleus and integrate into the genome of the target cell. In this integrated form, the viral genes are expressed. Integration of the viral genome into the target cell's genome is an essential part of its replication. Retroviral vectors are extremely efficient at infecting a wide variety of cell types, including primary cells from many tissues {McLachlin, J. R., et al., Prog. Nuc. Acid Res. Mol. Biol., 38:91–135 (1990)}. The major drawback of retroviral vectors is that mitotically active cells are required in order for the retroviral preintegration complex to enter the nucleus and integrate into the genome.

U.S. Pat. No. 5,256,553 to Overell discloses a retroviral vector containing three inserted genes (two oncogenes and at least one heterologous gene) each of which is independently transcribed in an infected cell under the control of its respective transcriptional control sequence. In its Example 1, the patent discloses primary rat embryo fibroblasts (REFs), Balb/3T3, and ψ2 (ψ2 is a retroviral packaging cell line derived from 3T3 cells) transformed by two triple promoter retroviral vectors each containing a v-Ha-ras oncogene, a v-myc oncogene, and a neomycin phosphotransferase (neo) gene which confers resistance to G418 antibiotic resistance. Example 2 of the patent discloses two other triple-promoter vectors, similar to those of Example 1 except that instead of the neo gene, these vectors contained hygro (hph) gene which conferred resistance to hygromycin B. The Example 2 vectors were used to transform Balb/3T3 and ψ2 cells. In Example 3 of the patent, the vectors of Examples 1 and 2 were transfected into ψ2 cells. Viruses harvested from the virus-producing clones were incubated with Balb/3T3 cells and found to be capable of infecting the cells. However, it must be noted that cellular transformation is a multistep genetic process in all species, but the process differs between human and rodents in the relative refractoriness of human cells to transformation. The reason for this difference is not known. Additionally, primary human cells are often relatively refractory to many methods of stable gene transfer. Together, these facts make the development of human cell lines in vitro difficult. Thus, most human cell lines have been derived from primary cancers that have been adapted to culture in vitro.

SUMMARY OF THE INVENTION

One aspect of the invention presents vectors containing two or more oncogenes under the control of one or more inducible promoters and/or genetic elements. The preferred vector contains two or more, preferably two or three, oncogenes under the control of one inducible promoter or two genetic elements. The inducible promoter provides a means for activating or suppressing the transcription and thus the expression of the oncogenes. The genetic element, preferably a pair of genetic elements flanking at least one (but preferably all) of the oncogenes, allows for the excision (removal) of the oncogenes from the vector or the genome or genetic sequence into which the vector has integrated. These vectors are preferably viral vectors capable of producing infectious, but replication deficient, viruses. The most preferred vectors are retroviruses. The vectors may further comprise genes coding for repressor(s) or activator (s) for the inducible promoter(s). These genes are hereinafter referred to repressor or activator genes, respectively. Alternatively, the vectors may contain binding site(s) in the inducible promoter(s) for such repressor or activator gene (s). The vectors may each additionally contain one or more desired genes which are expressed in the genetically modified cells.

Another aspect of the invention presents vectors containing an oncogene and a gene that encodes an effector of ras, where expression of the genes is under the control of an inducible promoter. In another aspect the vectors contain an oncogene and a gene that encodes an effector of ras, with a pair of recombination sites flanking at least one of the genes, such that one or all of the genes can be excised upon expression of a recombinase.

Another aspect of the invention presents a cell transfected by any of the vectors disclosed herein. Thus, in one embodiment, the cell is transfected with a vector comprising at least two oncogenes and a pair of recombination sites. The cells of the invention includes progeny of an initially transfected cell, such as cells in a cell line. In a preferred embodiment the cell is a mammalian cells, such as a human cell, such as a cell from human pancreas.

In another aspect the invention presents a mammalian cell comprising recombination sites not naturally found in the cell, wherein at least one oncogene lies between said recombination sites.

In another aspect the invention presents a non-naturally occurring cell produced by transforming a cell with one or more oncogenes, allowing the cell to divide at least once and removing the oncogenes from the cell by expressing a recombinase in the cell. In one embodiment the expression of the recombinase is under the control of an inducible promoter, such as a lac operator inducible promoter. In a preferred embodiment the recombinase is Cre recombinase or FLP recombinase.

In another aspect the invention presents a method for producing a non-naturally occurring cell comprising transforming a cell with a retroviral vector comprising at least one oncogene flanked by recombination sites, allowing the transformed cell to divide at least once, and introducing recombinase into the cell, whereupon the oncogenes are excised. In a preferred embodiment the recombination sites are from bacteriophage PI and the recombinase is Cre recombinase. In a second preferred embodiment the recombination sites are from FLP target sites and the recombinase is FLP. As noted above, the recombinase may be encoded by a gene under the transcriptional control of an inducible promoter such that the step of introducing the recombinase into the cell involves inducing transcription of the gene.

In a related aspect, the invention presents a cell produced by the methods disclosed herein. In preferred embodiments the cell is from pancreas, such as human pancreas, such as a pancreatic β-cell. In a preferred embodiment the cell produces insulin.

In a related aspect of the invention presents a method for producing cells useful for transplantation. The method uses the above vectors to transform target cells. In the genetically modified cells, the oncogenes are expressed and the cells allowed to multiply to establish a cell line. Once a sufficient number of cells are obtained, the inducible promoter(s) are repressed to suppress expression of the oncogenes or the oncogenes are removed. If the cells are precursor cells, they are then allowed to differentiate. The genetically modified, oncogene-suppressed or -removed, and/or differentiated cells are useful for transplantation into patients.

Another aspect of the invention presents cell lines produced by the above method.

Another aspect of the invention presents cell transplantation therapies by means of transplanting the above genetically modified, oncogene-suppressed or -removed, and differentiated cells into patients.

Another aspect of the invention presents non-naturally occurring human cell lines, with extended lifespan in vitro, transformed by one or more exogenous oncogenes under the control of one or more, preferably exogenous, inducible promoters. More preferably, the cell lines are transformed by at least two oncogenes. The preferred cell lines are human pancreatic cell lines. Most preferably, the cell lines produce insulin.

BRIEF DESCRIPTION OF THE DRAWINGS

FIG. 4 schematically presents the development of pseudotyped retroviruses LNSVoTPMPRL and LoTPM-PRRNLo FIG. 5 schematically presents the lac operator (O)-lac repressor (I) system.

FIG. 6 schematically presents the retroviral vector pLIS-VHygL containing LacI (lacI gene), SV (SV40 early promoter), hyg (hygromycin dominant selectable marker), and LTR (long terminal repeats).

DETAILED DESCRIPTION OF THE INVENTION

Figures 1A, 1B, 1C:
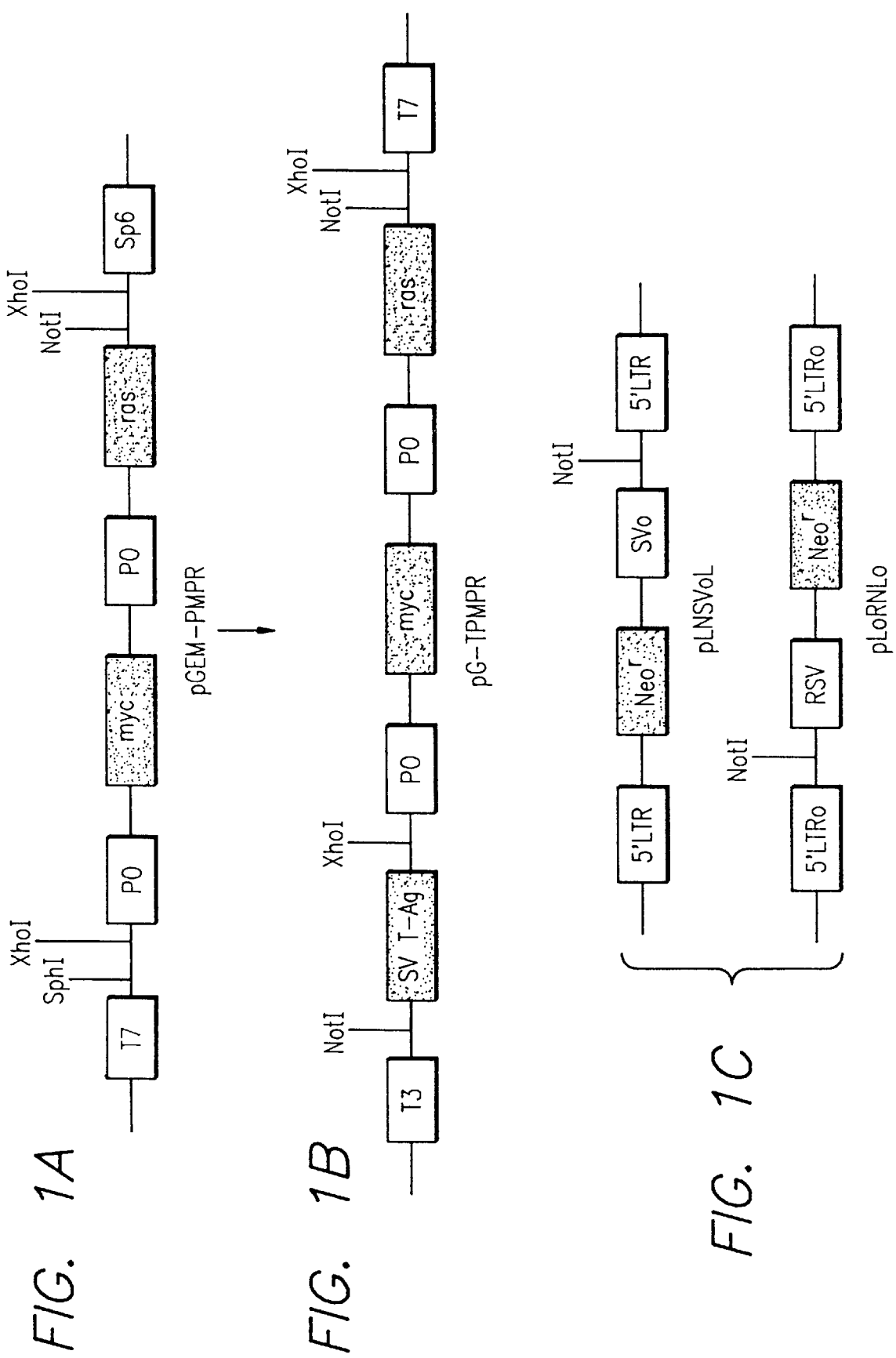
FIG. 1A shows plasmid pGEM-PMPR. Open boxes represent regulatory elements. Hatched boxes represent coding sequences. All circular plasmids are drawn in linear form and only the subcloned genes and their flanking elements are shown. The notations are as follows: SV-T or SV T-Ag (SV40 T antigen), myc (human c-myc), ras (H-ras$^{val12}$), neo or Neo$^r$ (neomycin resistance gene), LTR (retroviral long terminal repeat), LTRo (modified LTR containing lac operator sequence), SVo (modified SV40 promoter containing lac operator sequence), RSV (Rous sarcoma virus LTR promoter) and PO (poliomyelitis virus ribosomal internal entry sequence). Letters above the structure represent restriction enzyme sites: N (Not I), H (Hind III) and E (EcoR I). Arrows indicate expected transcription initiation sites. Scheme is not drawn to scale.
FIG. 1B shows plasmid pG-TPMPR. Notations are as in FIG. 1A.
FIG. 1C shows retroviral vectors pLSNVoL AND pLoRNLo. Notations are as in FIG. 1A.

As used in this application, the term "vector" refers to DNA or RNA vehicle, such as a plasmid, comprising nucleotide sequences enabling replication of the DNA or RNA in a suitable host cell, such as a bacterial host. In this invention, a vector includes a recombinant retrovirus containing oncogenes which are transcribed into mRNA and translated into proteins when the proviral sequence is expressed in the genetically modified target cell.

"Transfection" refers to the introduction of an exogenous nucleotide sequence, such as DNA vectors in the case of mammalian target cells, into a target cell whether or not any coding sequences are ultimately expressed. Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA. Genetic modification of the target cell is the indicia of successful transfection. "Genetically modified cells" refers to cells whose genotypes have changed as a result of cellular uptakes of exogenous nucleotide sequence by transfection. In will be appreciated that, as used herein, reference to "transfected cells" or "genetically modified cells" includes both the the particular cell into which a vector or polynucleotide is introduced and progeny of that cell. "Primary cells" are cells that have been harvested from the tissue of an organism.

One aspect of the invention presents vectors containing two or more oncogenes under the control of one or more inducible promoters and/or genetic elements, capable of expression in the cells they genetically modified. For example, each vector may contain two to five oncogenes under the control of one or more inducible promoters or genetic elements. More preferably, all the oncogenes are under the control of one inducible promoter or a pair of genetic elements. The most preferred vector contains two or three oncogenes under the control of one inducible promoter or a pair of genetic elements. The vectors also preferably contain repressor or activator gene(s) which interact with the promoter(s). Alternatively, the vectors may contain site(s) for the introduction of the repressor or activator gene(s). These vectors are preferably viral vectors, in which case the present invention also presents their recombinant viruses. Preferably, the oncogenes are dominant oncogenes. The recombinant viruses are preferably infectious but replication defective. The vectors are preferably capable of transfecting cells and stably expressing the oncogenes to enable growth of the cells for an extended period of time in vitro. The present invention is preferably directed to genetically modifying eukaryotic cells that are otherwise incapable of extended growth in vitro. The latter eukaryotic cells are preferably mammalian and more preferably human cells. In a one vector system, the vector may further comprise one or more genes coding for one or more proteins which repress or activate the inducible promoters. Alternatively, in a two-vector system, the vector may contain a site for such repressor or activator genes. The repressor or activator genes are subsequently introduced into the genetically modified cells by transfection by a second vector containing the repressor or activator genes. Specific examples of a one vector and two-vector systems are discussed in the section "Inducible Promoters And Genetic Elements", below. The vectors may each additionally contain one or more desired gene(s) which can be stably expressed in the cells genetically modified by them. The vectors can be introduced (transfected) into the target cells by any methods known in the art, such as those described above. The preferred vectors are viral vectors and the cells are preferably genetically modified by infection with infectious, but replication deficient, recombinant viruses. Retroviral vectors and retroviral-mediated gene transfers are the most preferred.

In the present invention, the vector may contain one oncogene. However, by using a vector containing two or more oncogenes under the control of preferably a single inducible promoter or a pair of genetic elements, the present invention possesses advantages over the prior art. Multiple genetic alterations may be needed for complete transformation. Efficient transformation may be achieved by oncogene cooperation {Hunter, T., Cell, 64:249–270 (1991)}. Transfer of oncogenes in separate vectors, especially in the form of plasmid transfection {Taylor, W. R., et al., Oncogene, 7:1383–1390 (1992); Spandidos, D. A., et al., Anticancer Res., 9:1149–1152 (1989)}, is much less efficient than simultaneous transfer of multiple oncogenes in a single retroviral vector. Previously, simultaneous transfer of oncogenes in retroviral vectors used separate promoters to drive each oncogene {Overell, R. W., et al., Mol. Cell. Biol., 8:1803–1808 (1988)}. However, this may lead to promoter interference {Emerman, M., et al., Nucl. Acid. Res., 14:9381–9396 (1986)}. In addition, no inducible promoter in two-oncogene vectors were available although such promoters were used in single oncogene system {Efrat, S., et al., Proc. Natl. Acad. Sci. USA, 92:3576–3580 (1995); Epstein-Baak, R., et al., Cell Growth Diff., 3:127–134 (1992)}. In the present invention, a single oncogene may be used, such as p53, if it will trigger the formation of oncogenes in the genes of the transfected cell.

Another aspect of the invention presents cell transplantation therapies using cells genetically modified by the above vectors. These cells are transplanted into a patient, e.g., to replace the destroyed or malfunctioning cells in the patient or to produce the desirable gene products. The genetically modified cells are preferably of the same species as the host into which they will be transplanted. Generally, mammalian target cells are used for treating mammalian subjects. Thus, in the case of a human patient, the cells are preferably human.

The target cells can be adult or precursor cells. Precursor cells are cells which are capable of differentiating, e.g., into an entire organ or into a part of an organ, such as cells which are capable of generating or differentiating to form a particular tissue (e.g., muscle, skin, heart, brain, uterus, and blood). Examples of precursor cells are endocrine precursor cells and fetal cells. Fetal cells are readily obtained and capable of further growth. In the case of recombinant retroviruses, fetal cells are still capable of division and can therefore serve as targets for these viruses. Adult cells can be coaxed to grow, for example, by growing them in the extracellular matrix from 804G cells and HGF/SF, or by exposing them to mitotic agents, such as collagenase, dexamethasone, fibroblast growth factor, before infecting them with the recombinant retroviruses. The expression of the oncogenes in the genetically modified target cells spur further cell growth for an extended period of time.

In a preferred embodiment the target cells are from human pancreas, which may be either fetal or adult. In one embodiment adult human islets are used (Wang et al., 1996, Diabetes 45 supplement 2:285A5, incorporated by reference herein in its entirety for all purposes). In a preferred embodiment the cells are purified $\beta$-cells. $\beta$-cells may be separated from non $\beta$-cells (such as $\beta$, $\delta$, and PP) found in human pancreas on the basis of cell properties, such as the ability of $\beta$-cells to accumulate flavin adenine dinucleotide (FAD) when incubated in a medium containing a low concentration of glucose. A useful method for purifying $\beta$-cells is by flow cytometry as described in the Examples, infra.

The present invention deals in particular with the novel infection of human cells and production of infected human cell lines that can grow in vitro for an extended period of time, such as for 50 cell divisions or for at least six months, more preferably for at least 150 cell divisions or 10 months, and most preferably at least a year. These cell lines are preferably transformed by the above vectors. In particular, the present invention discloses cell lines generated from the endocrine precursor cells of the human pancreas, and insulin-producing cell lines directly derived from human fetal pancreas, or fetal pancreas of any species. These insulin-producing cell lines are preferably derived from cells infected by retroviral vectors containing at least two oncogenes under the control of an inducible promoter. The preferred retroviral vector expresses SV40 T antigen and H-ras$^{val12}$, in the infected cells, under the control of a lac repressor-responsive promoter.

The inducible promoters and genetic elements in the vectors inducibly regulate the oncogene expression since the expression of multiple oncogenes in primary cells, e.g., endocrine precursor cells, would be likely to interfere with the ability of those cells to differentiate. Moreover, expression of the oncogenes in the host may cause tumor. Thus, once the number of the genetically modified cells have reached the desired amount for harvest, the oncogenes in the cells are then suppressed or removed, and precursor cells if present are allowed to differentiate into mature cells. These differentiated mature cells are then transplanted into the patient. Thus, regardless of the in vitro lifespan of the cell lines, the most preferred cell line presents non-dividing, preferably differentiated, human cell lines useful for transplantation, preferably because they produce a desired product.

There are two aspects to the cell transplantation. In the first aspect, the transplanted cells serve to supplement the cells that are destroyed, malfunctioning, or absent in the transplant patient. In the second aspect, the vector may contain a foreign gene expressing a desired product that is missing, malfunctioning or expressed at a low level in the transplant patient. In the second case, the transplanted cells express the desired gene product in the transplant patient.

In the practice of the first aspect of the cell transplantation therapy, the target cells are preferably those that are not regenerated in the patient. Thus, for example, human fetal neurons can be grown and multiplied in vitro by the above method and the oncogenic-suppressed or -removed, differentiated neurons transplanted into human patients. The patients are those suffering from loss of or dysfunctional neurons, such as patients suffering from: Alzheimer, Parkinson, and other neurodegenarative diseases. Similarly, human bone marrow or stem cells may be produced and transplanted into patients suffering from depressed immune response. These patients include those suffering from inherited defects, cancer, immunodeficiency syndrome (AIDS) or patients undergoing cancer therapy. Once in circulation, the transplanted bone marrow or stem cells travel to the bones where the immature cells grow into functioning B and T cells. Other fetal cells that may be used are endocrine secreting cells such as pituitary and hypothalamus cells, in particular, endocrine precursor cells, such as human fetal pancreatic (HFP) cells. The genetically modified and transplanted cells preferably supplement the transplant host's cells in the production of the needed endocrine hormones. Myoblasts can also be genetically modified, differentiated, and transplanted into patients suffering from loss of, malfunctioning, or degenerating muscle, such as patients suffering from cardiac disorder and muscular dystrophy. Other examples include transplantation of genetically modified, oncogene-suppressed or -removed, differentiated fetal pancreatic cells into human patient. Preferably, the transplanted cells secrete insulin in response to glucose level in the patient, in an amount and with the precise timing that is needed for control of glucose homeostasis. The vector may additionally contain one or more genes which encode a desired gene product. The desired gene product may be lacking, absent or defective in the transplant host. Thus, the transplanted cells, by expressing the gene product, supplement or overcome the transplant host's lack of the normal gene product. For example, the vector may additionally contain Factor IX gene which encodes a blood clotting factor. Once transplanted into a hemophilic patient, the resulting genetically modified cells produces the blood clotting factor in vivo to supplement the patient's blood clotting factor. In another example, the vector may contain a gene encoding dystrophin which is then used to genetically modified myoblasts or other cells for transplant into patients suffering from muscular dystrophy. In yet another example, to increase the production of neurotransmitters, neuronal cells are infected with the recombinant viruses containing the oncogenes, inducible promoter and one or more genes coding for neurotransmitters. Other examples of desirable genes are those which produce: immunoglobulins, serum proteins, viral or tumor cell antigens, or biologically active molecules such as enzymes, hormones, growth factors, or receptors for hormones or growth factors, or homologues of the foregoing. Examples of the desired genes also include non-mammalian genes, such as bacterial sequences encoding for cholesterol-metabolizing enzymes.

The present method allows for the establishment and extended growth of cell lines, particularly fetal cell lines, of genetically modified, oncogene-suppressed or -removed and differentiated cells that are well characterized and can thus be used on many human patients, without requiring a cell line tailored to each individual patient. Preferably, these cells lines are immortal.

To reduce immunorejection by the transplant patient, the preferred vector and virus may additionally contain genes which reduces immunogenecity in the genetically modified cell lines. An example of such a gene is the adenoviral P19 gene which encodes a transmembrane glycoprotein (gp19K). gp19K is localized in the endoplasmic reticulum and binds to class I antigen (Ag) of the major histocompatibility complex (MHC). This binding blocks the transport of class I Ag to the surface of the infected cell and prevents class-I-restricted cytolysis by cytotoxic T lymphocyte (CTL) {Paabo, S., et al., Cell, 50:311–317 (1987) and references within; Wold, W. S. M., and Gooding, L. R., Mol. Biol. Med., 6:433–452 (1989)}. With reduced immunogenicity, genetically modified cell line banks can be established to supply these cells for transplantation into e.g., human patients at treatment centers remote from the cell line banks. The availability of the cell lines and cell line banks also provide ready sources of the cells for use for other purpose known in the art, replacing scarce sources such as cadavers and fetal tissues.

Alternatively, to further reduce host versus graft immune rejection, one may use the patient's cells and coaxed their growth by exposing them to mitotic agents, such as collagenase, dexamethasone, fibroblast growth factor, before genetically modifying them using the methods of the present invention.

Besides transplantation, the genetically modified cell lines can be cultured and used to produce the desired gene products in vitro which are harvested and purified according to methods known in the art. If the genetically modified cells are used to produce the desired gene products in vitro, it is not necessary to incorporate inducible promoter(s) in the vectors as tumorigenicity, a concern for a transplant host, will not be a concern in this case.

The cell lines described herein also provide well characterized cells for other purposes such as for screening of chemicals which interact with proteins on the cells' surface, e.g., for therapeutic uses.

Viral Vector Selection

Retroviral vectors are the preferred vectors of this invention, though other viral vectors may be used, such as adenoviral vectors. Though adenoviral vectors have the advantage of not requiring dividing cells for transfection, they have a disadvantage in that they do not integrate into the genome, possibly making it more difficult to derive stable cell lines. Adeno-associated viral (AAV) vectors might also be used but have the disadvantage of a smaller packaging limit than retroviral vectors.

The retroviral vector can be any that are known in the art. Retroviruses to be adapted for use in accordance with this invention can be derived from many avian or mammalian hosts. However, a requirement for use is that the virus be capable of infecting cells which are to be the recipients of the new genetic material (oncogene and/or desired gene) to be transduced using the retroviral vectors. Examples of retroviruses include avian retroviruses, such as avian erythroblastosis virus (AMV), avian leukosis virus (ALV), avian myeloblastosis virus (ABV), avian sarcoma virus (ACV), Fujinami sarcoma virus (FuSV), spleen necrosis virus (SNV), and Rous sarcoma virus (RSV). Non-avian viruses include: bovine leukemia virus (BLV); feline retroviruses such as feline leukemia virus (FeLV) or feline sarcoma virus (FeSV); murine retroviruses such as murine leukemia virus (MuLV), mouse mammary tumor virus (MMTV), and murine sarcoma virus (MSV); rat sarcoma virus (RaSV); and primate retroviruses such as human T-cell lymphotropic viruses 1 and 2 (HTLV-1, 2), and simian sarcoma virus (SSV). Many other suitable retroviruses are known to those skilled in the art. A taxonomy of retroviruses is provided by Teich, in Weiss, et al., eds., RNA Tumor Viruses, 2d ed., Vol. 2 Cold Spring Harbor Laboratory, New York, pp. 1–16 (1985). Particularly preferred retroviruses for use in connection with the present invention are the murine retroviruses known as Moloney murine sarcoma virus (MoMSV), Harvey murine sarcoma virus (HaMSV) and Kirsten murine sarcoma virus (KiSV). The MoMSV genome can be obtained in conjunction with a pBR322 plasmid sequence pMV (ATCC37190), while a cell line producer of KiSV in K-BALB cells has been deposited as ATCC 163.3. A deposit of a plasmid (pRSVneo) derived from pBR322 including the RSV genome and a neo marker is available as ATCC 37198. A plasmid (pPBI01) comprising the SNV genome is available as ATCC 45012. For example, a retroviral vector may be constructed so as to lack one or more of the replication genes such as gag (group-specific antigen), pol (polymerase) or env (envelope) protein encoding genes. The resulting recombinant retrovirus would thus be capable of integration into the chromosomal DNA of an infected host cell, but once integrated, be incapable of replication to provide infective virus, unless the cell in which it is introduced contains another proviral insert encoding functionally active transacting viral proteins. Methods for producing infectious but replication deficient viruses are known in the art such as described in Mann, et al., Cell, 33:153 (1983) and Miller, et al., Mol. Cell Biol., 6:2895 (1986), hereby incorporated by reference in their entirety.

Oncogene Selection

The multiple, preferably dominant, oncogenes can be any that are known in the art. The oncogenes are preferably chosen, as is described in detail in the Examples, according to the synergy amongst them in cellular transformation, and their ability to transform the target cells. Further, the large sizes of some oncogenes may affect their inclusion on the same vector. In order to provide transforming capability, the RNA or DNA constructs of the present invention incorporate at least two or three oncogenes, which can be derived from viral, cellular genomes, mammalian or avian chromosomal RNA or DNA. Partial lists of oncogenes are provided by Bishop, et al., in Weiss, et al., eds., RNA Tumor Viruses, Vol. 1, Cold Spring Harbor Laboratory, New York, pp. 1004–1005 (1984), and Watson et al., Molecular Biology of the Gene, 4th Ed., Vol II (Benjamin Cummings, Menlo Park, Calif., USA) p. 1037. Included are the known oncogenes such as jun, src, yes, abl, fps, fes, fms, ros, kit, mos, raf, H-ras, K-ras, sis, SV40 T-antigen (SV40 T-Ag), Her2/neu, C-erbB2, C-erB3, myc, myb, fos, ski and erbA. Many oncogene products have tyrosine-specific protein kinase or serine/threonine protein kinase activity, or appear to be homologues of growth factors, growth factor receptors, or are nuclear proteins with unknown function. Many oncogenes can be obtained from public collections of deposited biological materials. Thus, v-raf is present in the plasmid pF4 deposited as ATCC 45010 {Rapp, et al., Proc. Natl. Acad. Sci. USA, 80:4218 (1983)}; v-myc$^{mc29}$ is available as ATCC 45014; and v-Ha-ras is a genetic component of ATCC 41047.

In a preferred embodiment the SV40 T-antigen and ras (e.g., ras$^{val12}$) oncogenes are used. Mutants of the SV40 T-antigen can also be used, for example mutants deficient in the ability to inactivate p300, pRb, or p53. Additional preferred oncogenes are those that act as downstream effectors of ras, particularly when used in combination with SV40-T antigen.

Downstream Effectors of Ras

In an alternative embodiment, pancreatic cells are transfected with a vector comprising at least one oncogene (e.g., SV40 T antigen) and a second gene encoding a downstream effector of ras, which may or may not be an oncogene. Expression (or increased expression) of downstream effectors of Ras is likely affect growth and differentiation of the cell in a manner similar to Ras expression, resulting in cells that exhibit immortalization (or extended in vitro growth) but not tumorigenicity. Examples of downstream effectors of ras include raf family members (e.g., raft), ral GTPase, phosphatidylinositol 3-kinase (PI3), members of the rho family of GTPases (e.g., rhoA, Rac, Cdc42), mitogen-associated protein kinases, and Ral (e.g., Ral guanine-nucleotide exchange factor Ral-GEF).

Inducible Promoters and Genetic Elements

The oncogenes in each vector are under the control of one or more and preferably at most two, inducible promoters or inducible genetic elements. More preferably, multicistronic transcriptional units are used to express all the oncogenes under the control of the same promoter.

Inducible promoters and inducible genetic elements are known in the art and can be derived from viral or mammalian genomes. Numerous examples of inducible promoters are known in the art, including lacO-containing SV40 promoter, lacO-containing LTR promoter, metallothionein promoter, and the TET promoter. There are numerous sources of SV40 DNA, including commercial vendors such as New England Biolabs, Inc., Beverly, Mass., USA.

In a preferred embodiment inducible genetic elements are used. When inducible genetic elements are used, the oncogenes are suppressed by excising them from the transfected cells. Typically, the genetic elements are recombination sites (i.e., sequence specific recombination sites) and introduction or activation of a site specific recombinase (e.g., expression of a gene encoding a recombinase) results in precise excision of the genetic material between the genetic elements. Depending on the placement of the recombination sites relative to coding sequences, the introduction of the recombinase may result in excision of one or all of the the oncogenes, or sequences such as promoter sequences required for oncogene expression. Thus, as used herein, the induction of inducible genetic elements refers to the introduction of factors (e.g., a recombinase) sufficient to result in excision.

Prefered examples of suitable recombination sites are the Cre/lox recombination system from the bacteriophage P1 and the FLP recombinase system (i.e., FLP recombinase and FLP recombinase target sites). The P1 Cre/lox system is described in, e.g., Dale et al., Proc. Natl. Acad. Sci. USA, 88:10558–10562 (1991), which is hereby incorporated by reference in its entirety. The FLP recombinase system is described in, e.g., Golic et al., 1996, Genetics 144:1693–711; Seibler et al., 1997, Biochemistry 36:1740–7; Aladjem et al., 1997, Mol. Cell. Bio. 17:857–61; Rossi et al., 1996, Current Biology 6:866–72; Buchholz et al., 1996, Nucleic Acids Research 24:4256–62.; Ludwig et al., 1996, Transgenic Research, 5:385–95.; Buchholz et al., 1996, Nucleic Acids Research 24:3118–9.; Dymecki, 1996, Proc. Nat'l. Acad. Sci. USA 93:6191–6; Dymecki, 1996, Gene, 171:197–201, each of which is hereby incorporated by reference in its entirety. It is expected that additional recombination systems suitable for use in this invention will be discovered in the future, and it will be appreciated that any recombination system that allows controlled excision of genetic material can be used to practice the present invention. It will be appreciated that the excision system chosen generally should not be responsive to a recombinase activity normally expressed in the host cell (e.g., a pancreatic 6-cell).

In one embodiment, a two-vector system is used. The first vector contains the oncogenes flanked by the genetic elements consisting of recombination sites. As used herein, the term "flanking" has its normal meaning, i.e., one genetic element positioned on one side (which can be described as 5' or 3', or distal or proximal) of a gene or genes and the second genetic element positioned on the other side. Usually the genetic elements and the oncogene are introduced using the same vector; thus typically the distance between the genetic elements will be less than about 1000 kilobasepairs (kbp) of each other, more often less than about 500 kbp, often less than about 200 kbp, most often less than about 50 kbp. After the first vector has transformed the target cells and the cells have multiplied to a desired number, a second vector is used to transfect the cells. The second vector encodes a recombinase (e.g., contains a Cre recombinase gene or a FLP recombinase) which, when expressed in the cells, will excise the oncogenes from the genome of the cells. Alternatively, a single vector system can be used in which the recombinase is introduced found on the vector carrying the oncogenes. In either the one- or two-vector systems the expression of the recombinase may be under the control of an inducible promoter as described supra. As noted above, additional excision systems or methods for introducing a recombinase will be apparent to those of skill. Moreover, it will be appreciated by those of skill that following excision of the oncogenes by recombination, usually all or part of at least one of the recombination sites will remain behind in the chromosome of the transfected cell and progeny (along with vector sequences not lying between the recombination sites).

In some embodiments, the vector contains both inducible promoter(s) and genetic element(s). In the simplest example, the vector contains an inducible promoter and a pair of genetic elements flanking the oncogenes. In this system, the inducible promoter may be used to gradually reduce the expression of the oncogenes, e.g., to gradually adapt the cells to the absence of oncogenic activities, before the genetic elements are manipulated to excise the oncogenes.

Construction of suitable vectors containing the desired oncogenes and inducible promoter and/or genetic element system employs standard ligation techniques. Isolated plasmids or nucleotide sequences are cleaved, tailored, and religated in the form desired to form the plasmids required. For example, useful plasmid vectors for amplifying the retroviral genetic elements in bacterial hosts prior to transfection are constructed by inserting a retroviral DNA sequence encoding the elements described previously in a vector including one or more phenotypic selectable markers and an origin of replication to ensure amplification within a bacterial host. A preferred prokaryotic host for vector amplification is *E. coli,* although others may also be employed as a matter of choice. The viral vectors such as the recombinant viruses can be used to transfect or infect cells, and the genetically modified cells selected for using methods known in the art, see e.g., Sambrook, J., et al., eds., Molecular Cloning: A Laboratory Manual, Cold Spring Harbor Laboratory Press, 2d ed. (1989). The genetically modified cells are cultured in conventional nutrient media modified as appropriate for activating or repressing the promoters, and selecting for genetically modified cells. The culture conditions are those suitable for the target cells and will be apparent to those skilled in the art.

Retroviral vectors capable of expressing multiple genes under the control of a promoter in eukaryotic cells are known in the art. For example, one method utilizes the ability of ribosome to reinitiate translation by a scanning mechanism after encountering a stop codon {Kozak, M., J. Biol. Chem., 108:229–41 (1989)}. This has been exploited to develop retroviral vectors in which two genes driven by the same promoter are efficiently expressed by being arrayed in close proximity {Levine, F., et al., Gene, 108:167–74 (1991)}. The second method utilizes a sequence from poliomyelitis virus to mediate internal ribosomal entry in mammalian cells so that multiple genes can be expressed from the same mRNA {Pelletier, et al., Nature, 334:320–25 (1988)}.

A number of different systems have been used to effect inducible oncogene function. If the genetically modified cells are to be transplanted, the inducible promoters must not be induced by conditions existing in the transplant host, such as the chemicals present in the host or the in vivo environment of the host. Temperature sensitive mutants of SV40 T-antigen have been used to effect inducibly transformed cell lines which have been transplanted in vivo and shown to differentiate and retain some normal functions {Chou, J. Y., Mol. Endocrinol., 3:1511–14 (1989)}. Ota and Varshavsky have developed a general method of generating temperature sensitive mutants {Ota, I. M., et al., Science, 263:1273–76 (1994)}. A drawback of temperature sensitive mutations is that the cells must be maintained at low temperature in order for the temperature sensitive protein to maintain normal function. Many primary cell types, including cells from the HFP, are intolerant to less than optimal temperatures. If the genetically modified cells are to be transplanted, the temperature of the transplant host must not induce expression of the oncogenes.

Another possible inducible system is to construct a fusion protein between the oncogene and a steroid hormone receptor. This has been shown to result in steroid inducible function of the fusion partner. Such a strategy has been used for both the myc and p53 oncogenes to achieve inducible transformation {Eilers, M., et al., Nature, 340:66–68 (1989) and Roemer, K., et al., Proc. Natl. Acad. Sci. USA, 90:9253–56 (1993)}. If the genetically modified cells are to be transplanted, the endogenous steroid level of the transplant host must not induce expression of the oncogenes. In addition, the host must avoid taking the amount of steroid which may induce oncogene expression. Due to these considerations, steroid inducible promoter system may not be the best system to employ.

Examples of other inducible promoters are metallothionein promoter, inducible by heavy metals {Mayo, K. E., et al., Cell, 29:99–108 (1982)}, the mouse mammary tumor virus (MMTV) promoter, inducible by glucocorticoid {Beato, M., et al., J. Steroid Biochem., 27:9–14 (1987)}, and the TET promoter which is repressed by tetracycline {Pescini, R., et al., Biochem. & Biophy. Res. Communications, 202(3):1664–7 (1994)}. Unfortunately, these systems suffer from significant problems. The metallothionein promoter has an unacceptably high level of basal expression in the absence of added heavy metals. The MMTV promoter has very low basal expression in the absence of added glucocorticoid but inducibility depends on the expression of sufficient levels of glucocorticoid receptor in the target cell. In vivo endogenous level of glucocorticoid poses a problem as it may activate the promoter and causes expression of the oncogenes. Further, although MMTV is a retrovirus, attempts to develop it into a vector for gene transfer have been hampered by difficulties in producing an efficient packaging cell line. In the present invention, the TET system has the disadvantage of requiring the transplant patient to take tetracycline or its analog to suppress the oncogenes.

In one embodiment, the lac repressor-lac operator inducible promoter system is used. In particular, the inducible promoter system from E. coli based on the DNA binding protein namely lac repressor (lacI), and the lac operator (lacO), has been shown to function in mammalian cells and consists of two components {Brown, M., et al., Cell, 49:603–12 (1987)}. The first consists of gene(s) of interest under the control of a promoter into which lacO has been introduced adjacent to the TATA box. The second component of the system is lacI gene. When expressed in the same cell, the lac repressor protein binds to the lac operator DNA sequence and acts as a potent inhibitor of transcriptional initiation and as a transcriptional terminator. In the present invention, the genes of interest are oncogenes.

As discussed above, the vector of the present invention can be constructed in two ways and the transformation of the target cells achieved via a one- or two-vector system, accordingly. The following uses the lac repressor-lac operator inducible promoter system in a retroviral vector to illustrate the one- and two-vector system which can be analogously applied to other repressor- or activator-promoter system.

In a one-vector system, the single vector is constructed to contain the oncogenes under control of the inducible promoter(s), and the repressor or activator gene.

In a two-vector system, the first vector contains an inducible promoter, controlling the multiple dominant oncogenes, into which the lacO sequence has been introduced. The second vector contains the lacI gene. Each vector contains a different dominant selectable marker, allowing for selection of a target cell which has been transfected by both vectors. Examples of the marker are those which introduce antibiotic resistance phenotype such as neo (G418 resistance), hygro (hygromycin resistance), or gpt (mycophenolic acid resistance). Other gene product markers and host strains include: thymidine kinase activity in tk- cells, or hypoxanthine phosphoribosyl transferase (HPRT) activity in HPRT-cells. Such selectable markers, as well as appropriate host cell lines for complementary markers, are widely available among researchers. A binding site for the repressor or activator gene is inserted into the first vector, e.g., in the LTR of the vector or in the promoter which controls the oncogene expression, before transfecting or infecting a cell line. For example, the LTR of the retroviral vector may incorporate an E. coli lac repressor binding site, allowing for the introduction of the lacI gene, e.g., through transfection by the second vector containing the lacI gene, into the cell line genetically modified by the first vector. Thus, the first vector has the potential for inducible regulation. The oncogene expression of the first vector is downregulated by introduction of the lac repressor gene into the genetically modified primary cell lines, with the goal of inducing differentiation of the cell lines into mature cells. Both the first and second vectors are preferably infectious, but replication-incompetent, retroviral vector and the transfection achieved by infection with these vectors.

Examples of vectors useful for the two-vector system are retroviral vectors containing the neo gene and lacO inserted into their promoters for regulating the oncogenes, such as retroviral vectors pLNSVoTPMPRL and pLoTPMPRRMLo. The second vector can be a retroviral vector expressing the lacI gene and a selectable marker different from neo gene; such as vector pLISVHygL, which expresses the hygromycin dominant selectable marker (hyg). FIG. 6 shows the construct of vector pLISVHygL. pLISVHygL was made by inserting lacI gene into the BamHI site of pLSHL, using method known in the art which is described in Sambrook, J., et al., eds., Molecular Cloning: A Laboratory Manual, Cold Spring Harbor Laboratory Press, 2d ed., (1989). pLSHL was a vector derived from Moloney murine leukemia virus and was provided by Dr. W. Sugden, McArdle Laboratory for Cancer Research, University of Wisconsin, Madison, Wis., USA. LacI gene was contained in pMTLacI {Figge, J., et al., Cell, 52:713–722 (1988)}, provided by Dr. David Livingston, Dana Faber Cancer Institute, Boston, Mass., USA. By sequentially introducing the inducible vector, followed by LISVHygL, a cell line can be derived in which the oncogenes can be induced by adding IPTG to the culture medium.

FIG. 5 shows an example of a two-vector system utilizing a lac operator (O)-lac repressor (I) system incorporated into a retroviral vector. LacI (I) binds tightly to the lacO sequence in the 5' long terminal repeat (LTR) and prevents transcription of the oncogenes of interest (X). Transcription of the downstream neo gene from an internal promoter (IP) is unaffected. Transcription can be induced by adding the galactose analogue isopropyl thiogalactopyranoside (IPTG) to the cells. IPTG binds to lacI, causing a conformational change leading to dissociation from the lacO sequence, thereby allowing transcription to occur. In a one-vector system, the same will be true except that the repressor is expressed by the same vector, and no second vector is used.

Thus, to develop cell lines suitable for transplantation into humans, human target cells can be infected by the first vector, such as LNSVoTPMPRL or LoTPMPRRMLo, in vitro. The target cells are preferably human fetal or precursor cells. The oncogenes are expressed in the infected cells and cause them to multiply and survive for an extended period of time in vitro. When the desired number of genetically modified cells has been obtained, the genetically modified cells are transfected, preferably infected, with the vector pLISVHygL. The cells are then selected in a medium containing hygromycin, G418, and IPTG. Clones resistant to both G418 and hygromycin are tested for oncogene expression in the presence and absence of IPTG, e.g., 20 mM IPTG. Oncogene expression can be tested for by many different techniques known in the art, including immunohistochemistry, Western Blotting, Northern Blotting, as well as by tests of tumorigenicity such as tumor formation in nude mice. Cell clones that exhibit tightly regulatable oncogene expression are selected and tested for their ability to differentiate, such as by transplantation under the kidney capsule of nude mice {using the method described in Beattie, G., et al., J. Clin. Endocr. Metab., 78:1232–40 (1994)}. The cells with the desired differentiated characteristics are selected. For example, the method may be used to produce cell lines suitable for transplantation treatment of IDDM, in which case the target cells are preferably human fetal pancreatic cells; and the genetically modified cell lines which stably express insulin at normal physiological level in response to glucose level in their environment are selected. Alternatively, it may be possible to introduce into these cells various genes that would confer on the cells the property of glucose-responsive insulin production. These genes can be inserted into one of the vectors used to transfect or infect the cells. When the differentiated cells are transplanted into a human host, the cells will not express the oncogenes as IPTG is absent in the body of the human host.

Examples of other retroviral vectors of the present invention include:

(1) the src, BCR-ABL, and Myb oncogenes, inserted into a retroviral vector, under the control of an inducible promoter (e.g., the lac operator-lac repressor system) or an excision system (e.g., Cre/lox or FLP). The resulting vector, preferably retrovirus, is used, e.g., to transform hematopoietic stem cells. The genetically modified, oncogene-suppressed, differentiated cells are useful for production of lymphokines or cytokines and transplant into patients suffering from, e.g., lack of or reduced immune cells or immune response, such as AIDS patients;

(2) dominant negative p53 mutant gene, the met oncogene, and the BCL2 gene, inserted into a retroviral vector, under the control an inducible promoter (e.g., the lac operator-lac repressor system) or an excision system (e.g., Cre/lox or FLP). The resulting vector, preferably retrovirus, is used, e.g., to transform human hepatocytes. The genetically modified, oncogene-suppressed, differentiated cells are useful for maintaining hepatic functions such as the production of clotting factors and transplant into patients suffering, e.g., from malfunctioning liver; and (3) the C-jun and k-ras oncogenes inserted into a retroviral vector, under the control of an inducible promoter (e.g., the lac operator-lac repressor system) or an excision system (e.g., Cre/lox or FLP). The resulting vector, preferably retrovirus, is used, e.g., to transform human fetal neuronal cultures. The genetically modified, oncogene-suppressed, differentiated cells are useful for transplant into patients suffering from neuronal cell damage, such as burnt or accident patients.

Clearly, in the above three examples, a retroviral vector containing two instead of three of the oncogenes exemplified may also be used. Further, a retroviral vector containing SV40T and H-ras under lac repressor-lac operator inducible promoter system, as described previously can be used in place of the retroviral vector stated in the examples. Additionally, a one-vector system may be used instead of the two-vector system.

It should be noted that the oncogenes need not be inducible or removed and the above promoter-repressor system need not be used if the viral vector contains a combination of oncogenes that result in immortalization (or extended in vitro growth) but not tumorigenicity, and the transformed cells produce the desired differentiated gene product. This is also true if after transplantation, the genetically modified cells are contained and do not escape into the rest of the host's body. For example, the genetically modified cells can be contained in a physical matrix and transplanted thus. The physical matrix allows exchange of proteins, fluids and nutrients between the genetically modified cells and the host, but does not allow the cells to escape into the other parts of the host's body. For example, the cells can be encapsulated in alginate-poly(amino acid) membrane {Soon-Shiong, P., et al., Proc. Natl. Acad. Sci. USA, 90:5843–5847 (1993)}.

Expression of Exogenous Transcription Factor Genes in Transformed Cells

In some cases it may be desirable to increase levels of a transcription factor in a cell (or progeny of a cell) transfected with a construct of the invention (e.g., comprising two oncogenes flanked by genetic elements) in order to increase expression of desired proteins (e.g., proteins, such as hormones, characteristic of a differentiated state). Typically this is accomplished by transfecting the cell with a promoter-linked polynucleotide encoding the transcription factor. As used when referring to transcription factors, the term "exogenous" refers to a transcription factor expressed from a recombinant gene (i.e., a DNA not naturally found in the wild-type host cell), without regard to whether or not the transcription factor itself is normally expressed in the wild type cell at some level or under some conditions. Examples of transcription factors especially preferred when the target cell is a pancreatic endocrine cell include PDX-1 (also known as IPF1/STF-1/IDX-1), a homeodomain-containing transcription factor that transactivates the insulin gene as well as playing a role in pancreatic morphogenesis (see e.g., Peers et al., 1994, Mol. Endocrinol. 8:1798; Jonsson et al., 1994, Nature 371:606; Ohlsson et al., 1993, EMBO J. 12:4251), pax-4 (Sosa-Pineda et al., 1997, Nature 386:399–402), and beta-2 (Naya F J et al., 1995, Genes and Development, 9:1009–19).

The following Example is presented to illustrate some aspects of the invention, and are not to be construed as limiting the scope of the invention.

EXAMPLES

Materials and Methods

The cells were grown in Dulbecco's Modified Eagle Media (DMEM) with 10% fetal bovine serum (FBS) in 37° C., 10% $CO_2$, unless otherwise noted. Similarly, unless otherwise noted, the laboratory techniques used herein were based on standard techniques described in Current Protocols in Molecular Biology, Ausubel, et al., ed. Wiley Interscience & Greene Publishing Assoc. (1987); and the cloning methods were based on the methods described in Sambrook, J., et al., eds., Molecular Cloning: A Laboratory Manual, Cold Spring Harbor Laboratory Press, 2d ed., (1989).

Immunohistochemistry (IHC) for SV-T was performed using the antibodies SV40 T-Ag (Ab-2) (Oncogene Science, Manhasset, N.Y., USA) and the streptavidin-biotin conjugated immuno-alkaline phosphatase technique as previously described {Erber, W. N., et al., Amer. J. Clin. Pathol., 88:43–50 (1987)}. $Ras^{val12}$-specific ELISA assay (Oncogene Science) was done according to the manufacturer's directions.

Southern and Northern blot analyses was performed as described in Sambrook, J., et al., eds., Molecular Cloning: A Laboratory Manual, Cold Spring Harbor Laboratory Press, 2d ed., (1989). RNase protection assay (RPA), and reverse transcription-polymerase chain reaction (RT-PCR) analysis were performed as described in Mally, M. I., et al., Ped. Res., 36:537–544 (1994).

DNA content analysis of propidium iodide labeled cells in suspension was carried out using flow cytometer.

EXAMPLE I

Construction of the Three-Oncogene Retroviral Plasmids

Each of the retroviral plasmids pLNSVoTPMPRL and pLoTPMPRRNLo incorporated three oncogenes under the control of an inducible lacO-containing promoter having lac repressor binding potential. In order to maximize expression of each oncogene, two internal ribosomal entry sequences were used: one mediating myc expression, and the other mediating ras expression. In pLoTPMPRRNLo, the LTR incorporates an E. coli lac repressor binding site, allowing for the introduction of the lacI gene into the transformed cell line, giving the vector the potential for inducible regulation. In pLNSVoTPMPRL, the lac repressor binding site is incorporated into the SV40 early promoter (SV). The retroviral vectors express SV40 T-antigen, myc genes, and H-ras containing the val12 activating mutation, as a multicistronic transcript from the retroviral LTR. The oncogenes were chosen based on the synergy between T-antigen, H-ras, and c-myc in cellular transformation, and their ability to transform epithelial cells {Bradbury, J. M., et al., Intl. J. Cancer, 48:908–15 (1991); Quaife, C. J., et al., Cell, 48:1023–34 (1987); Peacock, J. W., et al., Oncogene, 5:1769–74 (1990); Merz, V. W., et al., Mol. Endocrinol., 5:503–13 (1991) and Bartek, J., et al., Proc. Natl. Acad. Sci. USA, 88:3520–24 (1991)}. H-ras was chosen initially over K-ras despite the fact that K-ras is more commonly involved in pancreatic ductal cancer, because the synergy of H-ras with SV40 T-antigen and myc is better characterized. Some oncogenes would have been desirable choices because of their involvement in epithelial cell transformation, such as members of the EGF receptor family, were not chosen initially because their large size would make it more difficult to include other oncogenes in the same vector.

FIG. 1 schematically presents the construction of the vectors. The abbreviations used in FIG. 1 are as follows:

T7, Sp6, and T3—bacteriophage promoters

PO—poliovirus internal ribosomal entry sequence myc—c-myc oncogene ras—H-ras(val12) oncogene SV T-Ag—Simian Virus 40 Large T-Antigen LTR—long terminal repeats LTRO—LTR containing lacO sequence Neo$^r$—recombinant neo gene SVo—SV40 early promoter containing lacO sequence RSV—Rous sarcoma virus long terminal repeats which controls the neo gene.

Additionally, in FIG. 1, the numbers represent the approximate length in base pairs. The various restriction sites of SphI, XhoI, NotI, and KpnI are indicated.

The oncogene elements used in the vector construction are as follows: the Simian Virus 40 large T-Antigen (SV40 T-Ag) cDNA was derived from plasmid pTEX-XH (a gift from Dr. David Livingston, Dana Faber Cancer Institute, Boston, Mass., USA); human c-myc (myc) cDNA was derived from plasmid PCMV-HM; and v-H-ras (ras)(also referred to as "H-ras$^{val12}$") cDNA, which contains a mutation at the position 12 from glycine to valine, was derived from plasmid pCMV-rasv. Both plasmids pCMV-HM and pCMV-rasv were gifts from Dr. George C. Prendergast, Merck, Sharp and Dohme Research Laboratories, Department of Cancer Research, West Point, Pa., USA. The poliovirus internal ribosomal entry sequence (PO) was derived from plasmid pBS-PO {a gift from N. Sonenberg, McGill University, Quebec, Canada; the plasmid is also described in Pelletier, J., et al., Mol. Cellular Biol., 8:1103–1112 (1988)} which contained a 750 base pairs (bp) of PO fragment. The c-myc, v-H-ras and PO DNA fragments were first subcloned into the cloning vector pGEM-7ZF(+) (Promega, Madison, Wis., USA) in tandem with PO-myc-PO-ras (PMPR) as shown in FIG. 1A.

Figure 2:
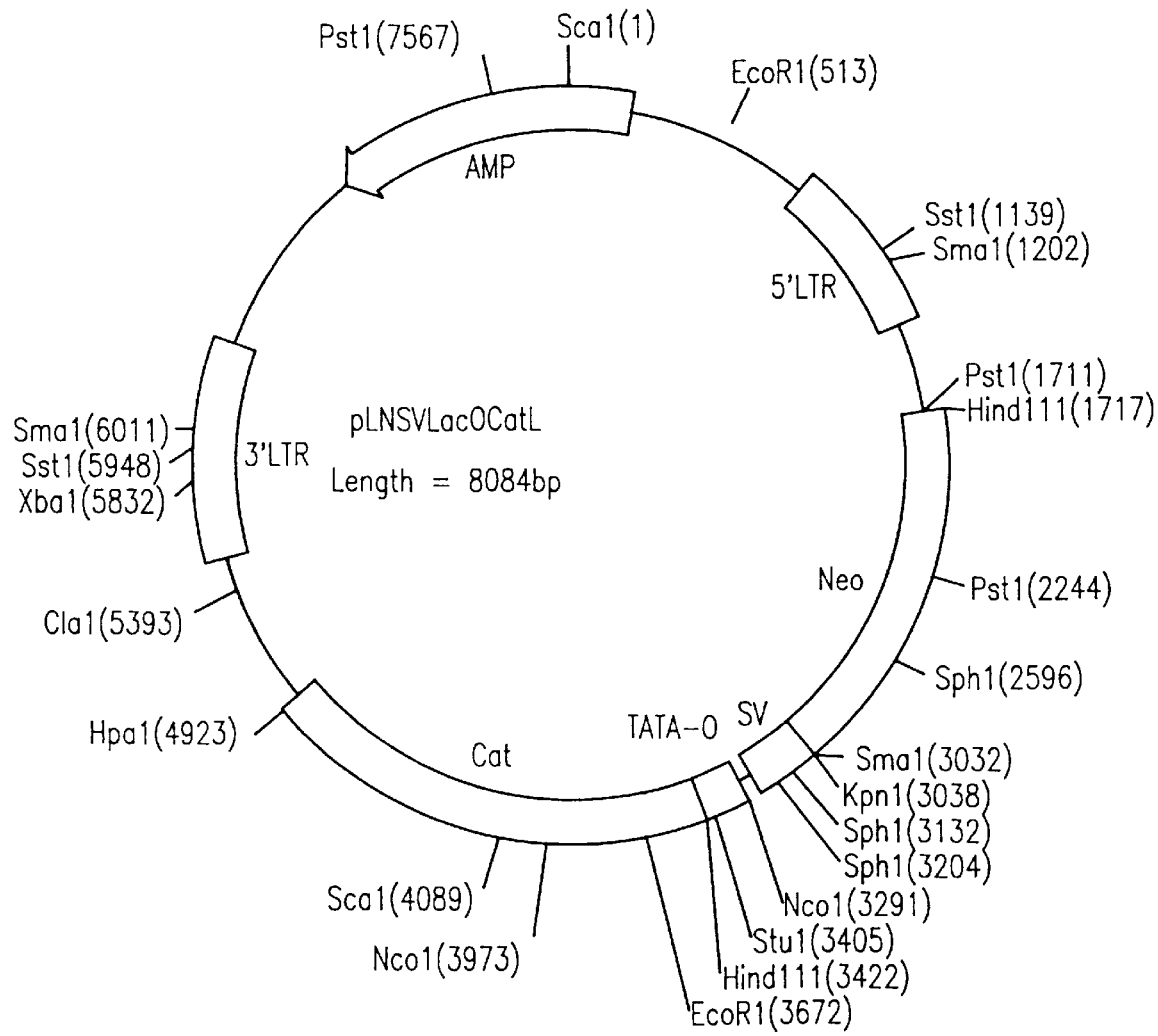
FIG. 2 schematically presents the restriction map of pLNSVLacOCatL.
Figure 3:
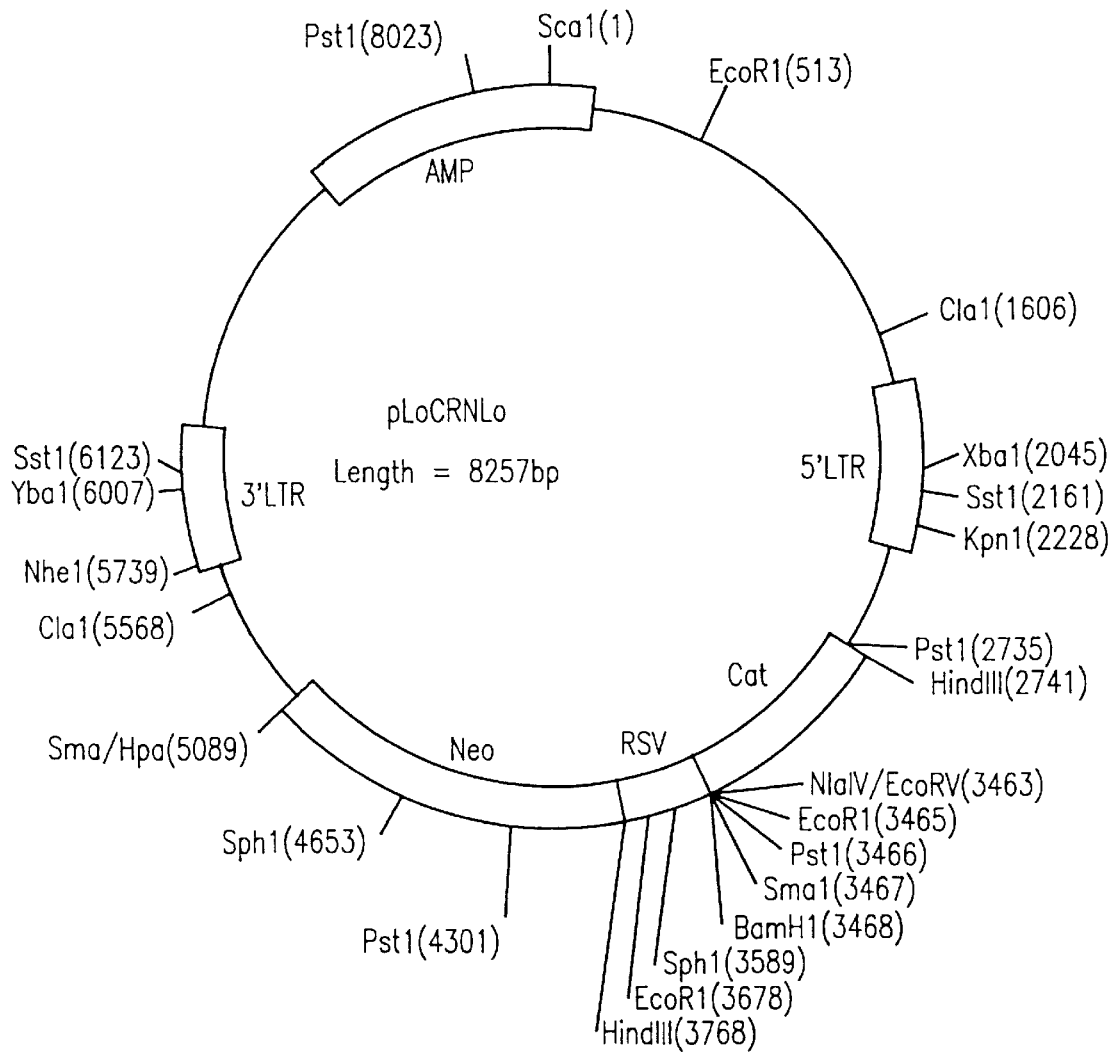
FIG. 3 schematically presents the restriction map of pLoCRNLo.

The resultant vector was named pGEM-PMPR. The PMPR fragment was then removed from pGEM-PMPR and subcloned into the XhoI site of pTEX-XH, downstream of the SV40 T-Ag cDNA, forming the plasmid pG-TPMPR (FIG. 1B). Two replication-defective Moloney murine leukemia virus-based vector plasmids, pLNSVLacOCATL and pLoCRNLo, containing respective lac operator sequence modified SV40 promoter and LTR with lac repressor binding potential were used as the starting parent vectors. The retroviral vector plasmid pLoCRNLo was derived from pLLRNL {Xy, L., et al., Virol., 171:331–341 (1989)} by replacing the luciferase gene (L) with chloramphenical acetyltransferase (CAT) gene (C), and by inserting an oligonucleotide containing a high affinity lac operator sequence {Brown, M., et al., Cell, 49:603–612 (1987)} into the SstI sites within the 5' and 3' LTRs, immediately 5' of the TATA box. The retroviral vector pLNSVoCL was derived from the MoMLV-based retroviral vector pLNLAL and pSVLacOCat {Brown, M., et al., Cell, 49:603–612 (1987)}. The SVLacOCat sequence was excised with KpnI and HpaI and cloned into pLNLAL by digesting PLNLAL with KpnI, which cuts immediately 3' of the neo gene (N), and HpaI, which cuts upstream of the 3' LTR. The structures of pLoCRNLo and pLNSVoCL are similar to those shown in FIG. 1 except for the presence of the CAT gene in place of the TPMPR cassette. A third vector, pLISVHygL, expressing the lacI gene (I) under the control of the 5' LTR and hygromycin resistance gene (hyg) under the control of the S40 early promoter (SV), was made by inserting the lacI gene into the retroviral vector plasmid pLSHL. The TPMPR fragment was removed from pG-TPMPR and subcloned into pLNSVoCatL and pLoCRNLo using NotI linkers, in place of the CAT gene. Accuracy of the subcloning process was examined by restriction mapping and Southern blot analysis of pLNSVoTPMPRL and pLoTPMPRRNLo using individual oncogene probes. The restriction maps of these vectors are shown in FIGS. 2 and 3, respectively. The lac operator was inserted into the SV40 promoter according to the method disclosed in Figge, J., et al., Cell, 52:713–722 (1988). The SV40 promoter containing the lac operator was then excised from the plasmid pSVlacOCAT (disclosed in Figge, J., et al., above) and inserted into the retroviral vector shown in FIG. 2. To produce the vector in which the lac operator was inserted into the LTR, oligonucleotides containing the lacO sequence {Figge, J., et al., above} and SstI cohesive ends were cloned into the SstI site adjacent to the TATA box in the 5' and 3' LTR promoters of the vector. Chloramphenical acetyltransferase gene ("Cat") was removed from the vectors to give rise to the new parent retroviral vectors, pLNSVoL and pLoRNLo (FIG. 1C).

Figures 1D, 8:
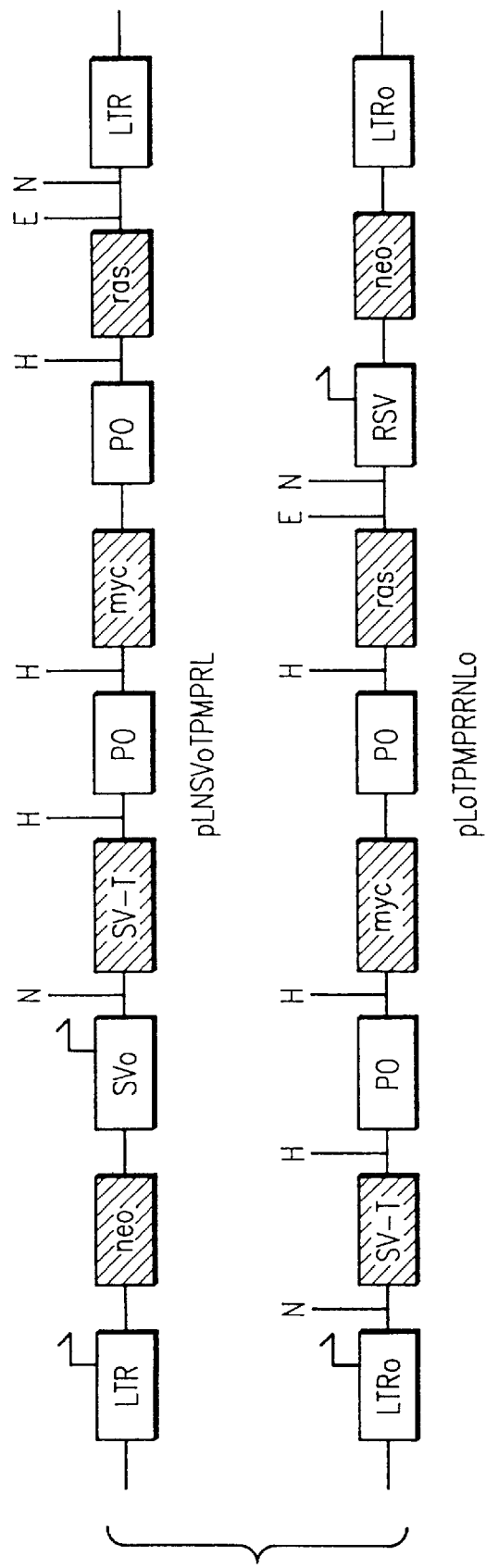
FIG. 1D shows retroviral vectors pLNSVoTPMPRL and pLoTPMPRRRNLo. Notations are as in FIG. 1A.
FIG. 8 schematically presents the provirus structure, drawn in linear form, in the producer cell line #4-11 and TRM-1 cells. Open and hatched boxes represent regulatory elements and genes to be expressed, respectively. The notations are as in FIG. 1. Letters above the structure represent restriction enzyme sites used in Southern blot analyses, H (Hind III), E (EcoR I), N (Not I) and P (PflM I).

The final three-oncogene retroviral vectors, pLNSVoTPMPRL and pLoTPMPRRNLo were obtained by subcloning the TPMPR fragment into the Not I site of each respective parent vector (FIG. 1D). Accuracy of the subcloning process was examined by digestions of vectors with multiple restriction enzymes after every step.

EXAMPLE II

Lac Repressor-Inducible Gene Regulation

The ability of LNSVoCL and LoCRNLo to mediate inducible CAT expression was tested in rat 208F cells. The cells were infected by one of the two CAT-expressing vectors followed by the lac repressor-expressing vector pLISVHygL. Infected cells were selected in media containing G418 and hygromycin. CAT activity in LNSVoCL-infected 208F clones was determined in the presence or absence of IPTG. Although there was significant variability in the extent of inducibility, some clones demonstrated 80–100 fold increases in CAT activity in the presence of IPTG over its absence, with very low basal CAT activity. Other clones showed high basal CAT activity, probably due to low levels of lac repressor expression or little CAT activity, reflecting instability of CAT expression from the retroviral vector. Similar results were found with LoCRNLo infected cells. This experiment demonstrates the feasibility of the use of lac operator modified promoters in retroviral vectors.

EXAMPLE III

Pseudotype Packaging Cell Lines

This example used vesicular stomatitis virus G-pseudotyped vectors to produce the infectious but replication deficient recombinant viruses LNSVoTPMPRL and LoTPMPRRNLo. Unless otherwise stated, the procedure used herein was based on the procedure disclosed in Burns, J. C., et al., Proc. Natl. Acad. Sci. USA, 90:8033–37 (1993). G-pseudotyped vectors have several advantages over conventional amphotropic MoMLV-based retroviral vectors. Unlike conventional retroviral vectors, G-pseudotyped retroviral vectors can be concentrated 100 to 1000 fold by ultracentrifugation to achieve titers of up to $10^9$ CFU/ml {Burns, J. C., et al., Proc. Natl. Acad. Sci. USA, 90:8033–37 (1993)}. Also, the host range of G-pseudotyped vectors is increased. Finally, the fact that 293GP cells {Viagene, Inc., La Jolla, Calif., USA; described and denoted 293-gag-pol in Burns, J., et al., Proc. Natl. Acad. Sci. USA, 90:8033–8037 (1993)} used herein do not produce any retrovirus until cultures are transfected with pHCMV-G {Yee, J., et al., Proc. Natl. Acad. Sci. USA, 91:9564–9568 (1994)} is of benefit in dealing with biohazard issues raised by retroviral vectors expressing multiple oncogenes. Virus titers of $10^4$ to $10^6$ CFU/ml were obtained by this method.

FIG. 4 schematically presents the development of pseudotyped retrovirus. The retroviral vector producer cell lines were produced using the formation of retroviral pseudotypes with the vesicular stomatitis virus G (VSV-G) protein {Burns, J. C., et al., Proc. Natl. Acad. Sci. USA, 90:8033–37 (1993)}. In this method, a retroviral vector plasmid and the plasmid pHCMV-G, expressing the vesicular stomatitis G protein from the strong CMV promoter, are co-transfected into 293GP cells which stably express the retroviral gag and pol genes. The 293GP cell line was derived from the human embryonal kidney cell line, 293 (ATCC CRL 1573). Upon introduction of the retroviral plasmid and VSV-G expressing plasmid, pHCMV-G, the 293GP cells gain ability to package the retrovirus through the VSV-G protein pseudotyping {Burns, J. C., et al., Proc. Natl. Acad. Sci. USA, 90:8033–37 (1993)}.

In this study, VSV-G pseudotyped retroviruses were produced by transiently transfecting 293GP cells with pCMV-G and pLNSVoTPMPRL or pLoTPMPRRNLo, using standard calcium phosphate precipitate procedure {Burns, J. C., et al., Proc. Natl. Acad. Sci. USA, 90:8033–37 (1993)}. Culture media containing the resulting viruses were collected daily from day 2 through day 4 after cotransfection. The media from each cotransfection were then pooled and used to infect fresh 293GP cells in the presence of 8 µg/ml of polybrene. Two days after infection, G418 was added to the medium to 400 µg/ml. G418 is an antibiotic that kills cells unless they express the neo gene. Approximately 10 days after initial infection, G418-resistant cell colonies were isolated and expanded.

The retroviral titer of these 293GP colonies was screened using baby hamster kidney (BHK) cells {BHK-21(C-31) cells designated ATCC CCL 10} that were infected with the pseudotyped retroviruses from the 293GP clones. BHK cells were chosen for screening because of their ease of transfection and infection. Two days after addition of the retroviral supernatants, the infected BHK cells were analyzed for SV40 T-Ag expression using immunohistochemical staining. The screening assay was repeated three times and the infectivity of each 293GP clone was estimated based on the percentage of positively stained cells. Two cloned producer cell lines, #10–2 (retrovirus LNSVoTPMPRL) and #4-11 (retrovirus LoTPMPRRNLo), were selected based on the high levels of SV-T protein in infected BHK cells. The titers of these clones, measured in 208F cells, were in the range of $5 \times 10^4$–$9 \times 10^5$ pfu/ml.

EXAMPLE IV

Effect of Oncogene-Expressing Retroviruses on Primary Human Fibroblasts

Since retroviral vectors in general have high mutation rate and these retroviral vectors contained complex multiple genes and duplicate copies of PO sequence, it was important to test the retroviruses not only by titer screening but also for transforming ability before submitting human fetal pancreatic cells to retroviral infection. Based on the estimated titer from BHK cells, three 293GP clones of LNSVoTPMPRL and fourteen 293GP clones of LoTPMPRRNLo were selected.

To test the transforming ability of the oncogene-expressing retroviral vectors, cells from the human primary fibroblast cell line, Basinger cells {a gift of Dr. D. Steinberg, University of California, San Diego, Calif., USA; also described in Levine, F., et al., Cell Transplant., 3:307–13 (1994), at passage 7, were seeded in 6-well plates at $10^5$/well and infected separately by these individual viruses at a multiplicity of infectivity (MOI) of approximately 0.5 in the presence of 4 µg/ml of polybrene. Two days later, the cells were placed in 400 µg/ml of G418 to select for infected cells. Seven days after infection, altered morphology in multiple foci started to appear. By day 16, cells were rounded-up, had an increased nucleus to cytoplasm ratio, and clear nucleoli. No G418-resistant cells maintained a normal morphology, demonstrating efficient morphological transformation induced by infection with the oncogene-expressing retrovirus.

Cells with the oncogene-containing retroviruses became pleomorphic, exhibited an increased nuclear to cytoplasm ratio, and grew on top of one another. In contrast, cultures infected with the control retrovirus, LZRNL, did not exhibit any morphologic differences from uninfected cultures. LZRNL is a moloney murine leukemia virus-based vector expressing reporter gene lac Z which encodes b-galactosidase {Xu, L., et al., Virology, 171:331–341 (1989)}. Additionally, cells infected with a vector expressing only SV40 T-antigen did not exhibit morphologic differences or focus formation in the time frame examined, demonstrating that a single oncogene is not sufficient to produce rapid, polyclonal transformation. Interestingly, although expressing the same oncogenes, i.e., SV-T and H-$\text{ras}^{val12}$, differences were noted between cells infected by retroviruses from producer clones #10-2 and #4-11. Compared to LoTPMPRRNLo (#4-11) infected cells, LNSVoTPMPRL (#10-2) infected cells were more pleomorphic, possibly due to promoter difference.

Generally, transformed cells are able to grow in media with reduced serum supplement. Infected Basinger cells maintain growth in media with reduced serum. In this study, growth rate of Basinger cells infected by LNSVoTPMPRL (#10-2) or LoTPMPRRNLo (#4-11) were measured in DMEM medium, supplemented with either 10% or 2% FBS. While 2% FBS greatly slowed down growth rate of control LZRNL infected Basinger cells, growth of LNSVoTPMPRL (#10-2) or LoTPMPRRNLo (#4-11) infected cells were not significantly affected by 2% FBS. The doubling time was approximately 30 hours.

EXAMPLE V

Infected Basinger Cells Have Lost Contact Inhibition In order to further characterize the degree of transformation of the infected Basinger cells, the ability of the infected cells to form foci in vitro was determined. This is a measure of loss of contact inhibition, a property commonly lost in transformed cells. After selection in G418, 20,000 cells were plated in a 10 cm plate and grown in DMEM with 10% FBS. Three weeks later the plates were stained with 5% Geimsa to visualize the cells. Control infected cells did not form foci, while oncogene-infected cells formed large numbers of foci. Compared to LZRNL-infected Basinger cells, LNSVoTPMPRL (#10-2) infected cells formed very distinct foci which were composed of morphologically heterogeneous cells, while #4-2 infected cells formed a smaller number of diffuse foci which were morphologically homogeneous.

EXAMPLE VI

Characterization of Infected Basinger Cells

Infected Basinger cells contain aneuploid DNA content. Oncogenic transformation, especially by SV-T, often results in aneuploidy. DNA content analysis showed that LZRNL-infected Basinger cells had a diploid DNA content of 2n, while LNSVoTPMPRL (#10-2)-infected Basinger cells had a significant subpopulation with an aneuploid DNA content. LoTPMPRRNLo (#4-11)-infected cells had a lower percentage of aneuploid cells than LNSVoTPMPRL (#10-2)-infected Basinger cells.

The infected Basinger cells were not immortalized. Although the infected Basinger cells possessed many properties of transformed cells, they still had a finite life span. Infected cells senesced after approximately 2 months (LNSVoTPMPRL, #10-2, infected) to 4 months (LoTPMPRRNLo, #4-11, infected) growth in culture. No attempt was made to maintain cells through crisis as is usually required to obtain immortalized cell lines.

The infected Basinger cells do not form tumors in nude mice. Tumorigenicity assays were conducted using three 6-week old NIH Swiss homozygous athymic nude mice which were obtained through the NIH Grantee Reimbursement Program from the Charles River Breeding Laboratories (Charles River, Mass., USA). They were housed in microisolater cages in a semisterile room. $2 \times 10^6$ cells were injected subcutaneously in the flank of thighs, totaling 6 injection sites, as previously described {Hayek, A., et al., Transplantation, 49:224–225 (1990)}. Animals were sacrificed two months later and examined for tumor development. Retrovirus-infected Basinger cells injected subcutaneously into the thighs of nude mice did not form tumors.

A significant feature of infection with LoTPMPRRNLo or LNSVoTPMPRL is that virtually all of the more than one-hundred colonies that arose from cultures infected with the oncogene-expressing retroviral vector exhibited morphologic changes. The data presented here demonstrate that the vectors of the present invention accomplished that goal.

The TRM-1 and TRM-6 cell lines described infra were derived from retroviral clone #4-11.

EXAMPLE VII

Oncogene Expression from the Recombinant Retroviruses

Because of the complexity of the oncogene-expressing retroviruses, it was important to examine oncogene expression. This was done initially using TRM-1, a cell line derived from human fetal pancreas by infection with retrovirus derived from the LoTPMPRRNLo producer clone #4-11. Northern blotting analysis with SV-T, myc and ras probes showed that SV-T and H-ras$^{val12}$, but not myc, were detected in the retroviral transcript, indicating that myc was deleted from TPMPR. Endogenous myc RNA was detected, indicating that the absence of myc hybridization to the retroviral transcript was not due to a technical problem with the Northern blot. Total RNA (30 mg each) was subjected to standard Northern blot analysis procedure and hybridized with respective 32p labeled probes of SV-T, myc and ras. 28S rRNA is visualized by nonspecific hybridization.

The absence of retroviral myc expression was investigated by Southern blot analysis of TRM-1 genomic DNA. TRM-1 (20 mg) and pLoTPMPRRNLo (20 pg) were digested to completion by NotI and then subjected to standard Southern blot analysis procedure, and hybridized with $^{32}$P-labeled SV-T probe. The provirus in TRM-1 was found to be shorter than the original retroviral plasmid. The shortened provirus was also found in producer cell lines #4-11 (LoTPMPRRNLo) and #10-2 (LNSVoTPMPRL), suggesting that the rearrangement occurred in producer cell lines. Based on further exhaustive Southern blots with various restriction enzymes and SV-T, myc, ras and PO probes, the structure of rearranged provirus in #4-11 and TRM-1 cells was confirmed to have myc and one PO sequence deleted (FIG. 8). The mechanism of rearrangement is thus most likely to have been a recombinational event between the two PO sequences.

Due to the concern that the rearrangement might have affected the expression of the remaining SV-T and H-ras$^{val12}$ genes, the presence of the protein products of these genes was examined. IHC assay detected nuclear SV-T protein in retroviral producer lines, #4-11 and #10-2 and corresponding infected Basinger cells. H-ras$^{val12}$ expression was analyzed by an ELISA highly specific for ras$^{val12}$ proteins. Ras$^{val12}$-specific ELISA (Oncogene Science) was performed according to the manufacturer's instructions. Control cell lysates were from cells containing ras proteins with known mutations, i.e., val12, arg12, and asp12, provided by the manufacturer. Basinger primary human fibroblasts, and 293GP retroviral packaging cells, were also used as negative controls. The signal was elevated several fold in #10-2 and #4-11 packaging cells as compared to the uninfected Basinger and 293GP cells.

In this Example, the PO elements recombined, resulting in deletion of the intervening myc gene. To avoid deletion, one may use other internal ribosome entry sequences that are not homologous with each other, i.e., the cap-independent translation enhancer of encephalomyocarditis virus {Parks, G. D., et al., J. Virol., 60:376–384 (1986); Jang, S. K., et al., J. Virol., 62:2636–2643 (1988)}, or polycistronic retroviral vectors can be constructed in which the coding sequences are placed in close proximity so that the downstream gene is translated by a ribosome scanning and translational reinitiation mechanism {Levine, F., et al., Gene, 108:167–174 (1991)}.

EXAMPLE VIII

Isolation of HFP

Epithelial cells harvested from pancreas are usually contaminated by stromal cells which form the supportive structure of the pancreas. When grown in fetal bovine serum, HFP epithelial cells have a low mitotic index {Otonkoski, T., et al., Transplant. Proc., 26:3334 (1994)}, and applicants' preliminary experiments indicate that the efficiency of retroviral infection is low. Experiments in which amphotropic retroviral vectors were used to infect mixed cultures of epithelial and stromal cells demonstrated that the stromal cells were infected much more efficiently than epithelial cells. Therefore, it was important to start with cultures that were as epithelial-enriched as possible. There are several methods to select epithelial over stromal cells. One method is based on the high level of endogenous 0-galactosidase in epithelial cells of HFP {Beattie, G., et al., J. Clin. Endocr. Metab., 78:1232–40 (1994)}. Using a lipophilic, fluorescent β-galactosidase substrate, β-galactosidase-positive cells can be isolated by fluorescent activated cell sorting. However, though this method is ideal in term of the purity of the cell population obtained, it results in a large loss of cells and a decrease in viability of the remaining cells, which are isolated as a single cell suspension. An alternative method is based on the finding that HFP epithelial cells express high levels of β1 integrins compared to stromal cells {Levine, F., et al., Cell Transplant., 3:307–13 (1994)}. Invasin, a protein produced by enteropathogenic Yersinia, binds tightly to β1 integrins and mediates the entry of the bacteria into epithelial cells. Therefore, purified invasin protein is used to isolate islet-like cell clusters (ICCs) that were enriched for epithelial cells {Levine, F., et al., Cell Transplant., 3:307–13 (1994)}. Epithelial-enriched ICCs are smaller and more translucent than ICCs containing many stromal cells, allowing them to be distinguished morphologically. The ability to isolate relatively pure populations of pancreatic epithelial cells enabled retroviral infection of cell populations containing very few stromal cells.

The present invention found that growth factor/scatter factor (HGF/SF) is strongly mitogenic for epithelial cells in the human fetal pancreas (HFP). 804G cells are from a bladder carcinoma cell line that has been found to produce an extracellular matrix that supports the growth of pancreatic epithelial cells better than any other source of extracellular matrix {Langhofer, M., et al., J. Cell. Sci., 05:753–64 (1993)}. Thus, in this example, the epithelial cells were initially grown in the extracellular matrix from 804G cells and HGF/SF in DMEM, supplemented with 10% fetal bovine serum, at 37° C. and 10% $CO_2$. In this growth condition, the epithelial cells formed an islet-like cell cluster (ICC)-derived monolayer cultures having a doubling time of 48 hours. With such high percentage of mitotically active cells, the use of retroviral vectors which require mitotically active cells for successful integration of viral DNA become attractive. After retroviral infection, the epithelial cells were grown in DMEM, supplemented with 10% fetal bovine serum, at 37° C. and 10% $CO_2$, without the extracellular matrix from 804G cells and HGF/SF. The use of HGF/SF offers an added advantage of selecting for epithelial over stromal cells. Stromal cells produce the growth factor HGF. Stromal cells do not express the HGF/SF receptor, the c-met proto-oncogene, and so do not respond to HGF/SF. Thus, HGF/SF treatment results in selective growth of the epithelial cells but also increases the mitotic index of the epithelial cells. The following method used the HGF/SF method.

In short, the human fetal pancreata used in these experiments were procured, after informed consent, by the International Institute for the Advancement of Medicine (Exton, Pa., USA) and Advanced Bioscience Resources (Oakland, Calif., USA). Pancreata were obtained after pregnancy termination by dilatation and extraction. Digestion and culture of the tissue was carried out as described in Beattie, G., et al., J. Clin. Endocr. Metab., 78:1232–1240 (1994); Otonkoski, T., et al., Diabetes, 43:947–953 (1994); and Hayek, A., et al., Ped. Res., 37:62A (1995). Cell lines were grown in RPMI 1640 plus 10% fetal bovine serum at 37° C. and 5% $CO_2$, unless otherwise noted. Cells were passaged at confluence at a 1:10 dilution.

In more detail, fresh 18 week and 24 week human fetal pancreases (HFP) were used. After dissecting away extraneous tissue from the HFP, the tissue was insufflated with HBSS (Hanks' Balanced Salts from Sigma Chemical Company, St. Louis, Mo., USA) using a 27 gauge needle. Following distension, the tissue was cut into several pieces and then digested in HBSS containing 3 mg/ml collagenase P (Boehringer Mannheim, Indianapolis, Ind., USA) for 20 minutes. After washing with HBSS, the preparation was stained with dithizone (DTZ; Sigma Chemical Company, St. Louis, Mo., USA) for selective identification of insulin containing cells {Latif, Z. A., et al., Transplantation, 45:827–830 (1988)}. Using the stain, between 200–500 fetal ICCs were picked by direct vision under a stereoscope. Insulin content/DNA (islets versus ICCs) in fresh preparations differed by a factor of 5, showing a significant enrichment for 0-cell in the DTZ-positive cell population.

Monolayer cultures of the dithizone-positive ICCs that had been carefully selected to minimize the number of stromal cells were infected with LoTPMPRRNLo or LNS-VoTPMPRL in the presence of HGF/SF at 0.5 MOI. Three days following infection, cultures were stained for the presence of SV40 T-antigen, demonstrating that a significant number of cells were infected. Approximately one week following infection, foci of cells with altered morphology, smaller and more refractile, became visible. These foci increased in size, indicating infected cell clones. This was confirmed with SV40 T-antigen staining. Groups of cells with altered morphology were subcultured to establish a cell line. However, initial attempts were unsuccessful because the cells developed numerous vacuoles, that gradually filled the entire cytoplasm, resulting in growth arrest and cell death. Electron microscopic analysis of these cells revealed that the vacuoles had a morphology consistent with lipid-containing structure In light of the lack of success in developing a cell line by subculturing, infected large monolayer cultures containing approximately six ICCs cultured together, were infected with the viruses, without any attempts at subculturing. Twenty-two days following infection, a culture infected with LoTPMPRRNLo (retroviral clone #4-11) became overgrown with a predominant cell type, designated TRM-1, for SV40 T-antigen, Ras, and Myc. TRM-1 was derived from an 18 week fetal pancreas. Some clones derived from TRM-1 have a morphology which more closely resembles primary epithelial cells from the HFP.

EXAMPLE IX

Characterization of TRM-1 Epithelial Markers

Stromal cells do not secrete insulin, whereas some epithelial cells do. Because it is impossible to derive absolutely pure cultures of epithelial cells from the HFP, the first important question in characterizing TRM-1 was to determine whether it was derived from the epithelial or stromal cells of the HFP. TRM-1 was derived from an 18 week fetal pancreas. At this stage of development, only 3% of pancreatic cells express insulin {using the method for detecting cells expressing insulin described in Beattie, G., et al., J. Clin. Endocr. Metab., 78:1232–40 (1994)}.

TRM-1 is positive for EP4 antigen {determined by the method described in Latza, U., et al., J. Clin. Pathol., 43:213–19 (1990)}, EP-CAM antigen {determined by the method described in Litvinov, S. V., et al., J. Cell Biol., 125:437–46 (1994)}, and the HGF/SF-receptor met gene expression {determined by the method described in Tsarfaty, I., et al., Science, 257:1258–61 (1992)}, properties which firmly identify it as an epithelial cell. Further, TRM-1 expresses cytokeratin, which is found only in epithelial cells. The epithelial associated glycoprotein EP4 is highly expressed in TRM-1 {Litvinov, S. V., et al., J. Cell Biol., 125:437–446 (1994)}. E-cadherin and N-CAM, which are known to be expressed in pancreatic islet cells {Rouiller, G. D., et al., Exp. Cell Res., 191:305–312 (1990); Rouiller, D. G., et al., Dev., 148:233–242 (1991)}, are also present in TRM-1, but at lower levels. The pattern of integrin expression in TRM-1 was similar to that of primary HFP epithelial cells, although there were quantitative differences in the level of expression of individual integrins. Table 1 summarizes some of the genes expressed by TRM-1.

TABLE 1

GENES EXPRESSED IN TRM-1

| Marker | Method | TRM-1 | HFP Epith. | HFP Stroma | Adult Islet |
|---|---|---|---|---|---|
| HGF/SF | RPA | − | − | + | − |
| met | RPA | + | + | − | + |
| β-gal | Hist./RPA | + | + | − | − |
| E-cadherin | IHC/FACS | + | + | − | + |
| EP4 | IHC/FACS | + | + | − | + |
| vimentin | IHC | + | + | ND | ND |
| cytokeratin | IHC | + | + | ND | ND |
| insulin | RIA/RPA | + | + | − | + |
| glucagon | RPA | − | + | − | + |
| glut2 | RT-PCR | + | + | − | + |
| glucokinase | RT-PCR | − | + | − | + |
| EP-CAM | FACS | + | + | − | + |

The expression of genes that are found in the cells of Table 1 was measured by a number of different techniques. RPA denotes RNase protection assay. "Hist" denotes histochemistry. "FACS" denotes flow cytometry. "IHC" denotes immunohistochemistry. "RIA" denotes radioimmunoassay. "RT-PCR" denotes reverse-transcription followed by polymerase chain reaction. "β-gal" denotes β-galactosidase gene. "Epith." denotes epithelial cells. "ND" denotes not done.

RNase protection assays on TRM-1 used total cellular RNA. Positive controls were total cellular RNA from: fetal pancreatic cell monolayer culture, ICCs, 22–24 week gestation total human fetal pancreatic tissue, adrenal gland. RNA was separately hybridized with the following respective probes: glucagon; insulin; somatostatin; IPF-1/STF1; c-met; HGF/SF; and TH. Cyclophilin expression measured on the same sample served as an internal control. Different amounts of RNA were sometimes used to detect low levels of mRNA. Yeast tRNA was run in parellel in all assays as a negative control and was always negative. RT-PCR assays on TRM-1 used positive controls of RNA from: ICCs and 18 week gestation human fetal pancreatic tissue. Primers for glucokinase and glut-2, which spanned introns were used to distinguish amplification products resulting from contaminating genomic DNA in the RNA samples.

Immunohistochemistry and B-galactosidase histochemical staining of monolayer cultures was done as described in Erber, W. N., et al., Amer. J. Clin. Pathol., 88:43–50 (1987); Beattie, G., et al., J. Clin. Endocr. Metab., 78:1232–1240 (1994). Primary antibodies were: SV40 T-Ag (Ab-2); polyclonal guinea pig anti-porcine insulin, rabbit anti-glucagon (Chemicon, El Segundo, Calif., USA); rabbit anti-human somatostatin. Normal rabbit or mouse serum were used as controls.

Flow cytometry was conducted as follows. Sub-confluent TRM-1 cell monolayers were dissociated into a free cell suspension by non-enzymatic dissociation medium (Sigma Immunochemicals, St. Louis, Mo., USA), washed in HBSS (3% FCS, 0.1% Na azide, and 0.2 mM EDTA) and incubated for 60 minutes at 4° C. first with primary antibodies specific for either E-cadherin (clone DECMA-1), NCAM (clone ERIC-1), or EGP40 (mnAb 323A3), used at a concentration of 10 mg per $10^6$ cells. Following extensive washes, samples were incubated with appropriate FITC-F(ab')2 secondary Abs. Samples to be assayed for cytokeratin-7 were first fixed and permeabilized by overnight incubation in 70% ethanol at 4° C., washed in HBSS (3% FCS, 0.1% Na azide, and 0.2 mM EDTA), and incubated with either an FITC-conjugated anti-cytokeratin-7 mnAb (clone LDS-68), or with FITC-conjugated control IgG1 mouse isotype. Following extensive washes samples were analyzed in a FACScan flow cytometer (Becton Dickinson, Mountain View, Calif., USA).

For double immunofluorescence for cytokeratins and insulin, sub confluent TRM-1 cell monolayers were washed with PBS and fixed in freshly made 4% formaldehyde (from paraformaldehyde) for 20 minutes at 4° C., permeabilized in 0.1% saponin for 10 minutes at room temperature, and then incubated in 50 mM glycine in PBS to saturate reactive groups generated by formaldehyde fixation. Nonspecific binding was blocked by incubation in PBS containing 2% donkey normal serum (Jackson Immunoresearch Lab. Inc., West Grove, Pa., USA) and 1% BSA (fraction V, Sigma Immuno Chemicals, St. Louis, Mo., USA) for 1 hour at RT. Following extensive washes in PBS (0.2% DS, 0.1% BSA), monolayers were incubated for 1 hour at room temperature with a mixture of primary antibodies: IgG fraction of a sheep anti-human insulin polyclonal antiserum (The Binding Site, Birmingham, England); mouse anti-pan cytokeratin (C9687, Sigma). In separate samples, a mixture of normal sheep, and mouse IgGs was used as control reference for specificity of primary antibodies. After several washes in PBS (0.2% DS, 0.1% BSA), cell monolayers were incubated for 1 hour at room temperature with a cocktail of secondary antibodies (Jackson Immunoresearch Lab. Inc.): LissamineRhodamine (LRSC)-conjugated affinity-purified donkey anti-sheep IgG (H+L) (preadsorbed on chicken, guinea-pig, hamster, horse, human, mouse, rabbit, and rat serum proteins; Jackson Immunoresearch Lab. Inc.); Fluorescein Isothiocyanate (FITC)-conjugated affinity-purified donkey anti-mouse IgG (H+L) (preadsorbed on bovine, chicken, goat, guinea-pig, hamster, horse, human, rabbit, rat and sheep serum proteins). Following six washes of 5 minutes each with PBS (0.2% DS, 0.1% BSA), samples were mounted in slow fade medium (Molecular Probes, Eugene, OR), and viewed on Zeiss Axiovert 35M microscope, using a 40X 1.3 NA objective lens, equipped with a laser scanning confocal attachment (MRC-1000, Bio-Rad Laboratories, Cambridge, Mass., USA). Fluorescent images relative to each marker were collected by using an argon/krypton mixed gas laser. Color images were printed on a Tektronix Phaser II-SDX.

Levels of insulin and glucagon released into medium and the corresponding hormone content of acid ethanol extracts of sonicated cells were measured by radioimmunoassay (RIA) as described in Otonkoski, T., et al., J. Clin. Invest., 92:1459–1466 (1993).

Subclones of TRM-1 have been isolated which have a morphology more closely resembling that of primary HFP epithelial cells in that they were flatter, have a decreased nuclear/cytoplasm ratio and exhibit more of the perinuclear granularity found in primary cells. Interestingly, these clones, which were originally selected only on the basis of morphology also exhibited increased expression of both EP-CAM and E-cadherin by FACS.

Endocrine Precursor Markers

β-galactosidase is expressed at high levels in TRM-1 (FIG. 31 PNAS). This enzyme is expressed at high levels only in HFP epithelial cells, particularly in endocrine precursors, and not in stromal cells or adult epithelial cells {Beattie, G., et al., J. Clin. Endocr. Metab., 78:1232–40 (1994)}. The data indicates that TRM-1 is derived from an epithelial cell of the HFP. Tyrosine hydroxylase, which is expressed in at least some β-cell precursors and is limited to a subset of the epithelial cells expressing high levels of β-galactosidase, was not detected in TRM-1 by IHC using an anti-TH antibody {Beattie, G. M., et al., J. Clin. Endocr. Metab., 78:1232–1240 (1994)} or by RPA.

Glucose Transport, Sensing and Islet Cell Antigens

GLUT-2, but not glucokinase, is detectable in TRM-1 by RT-PCR. TRM-1 cells do not express glutamic acid decarboxylase {Petersen, J. S., et al., Diabetes, 42:484–495 (1993)} by RPA and IHC but do express ICA69 {Pietropaolo, M., et al., J. Clin. Invest., 92:359–371 (1993)} by RPA.

Transformation State and Growth Characteristics of TRM-1

TRM-1 cells grow well in vitro, with a doubling time of approximately 36 hours. They grow well in low serum (DMEM, supplemented with 2% FCS) compared to control fibroblasts. Unlike primary epithelial cells of the HFP, TRM-1 is not dependent on exogenous extracellular 804G matrix or HGF/SF for growth in vitro. However, it does retain expression of the met proto-oncogene, which is the receptor for HGF/SF.

However, after approximately 150 cell divisions, passage 45, or more than 10 months in culture, slowing of cell growth was observed, suggesting that the cells have an extended lifespan. Similar to primary ICCs, TRM-1 cells can be grown in suspension culture, forming structures closely resembling ICCs and reaggregated primary HFP epithelial cells.

To further evaluate the tumoregenicity of TRM-1, six week old NIH Swiss homozygous athymic nude mice were obtained through the NIH Grantee Reimbursement Program from the Charles River Breeding Laboratories (Charles River, Mass., USA). They were housed in microisolater cages in a semisterile room. $5 \times 10^5$ TRM-1 cells at passage 10 were implanted under the kidney capsule as described in {Hayek, A., et al., Transplantation, 49:224–225 (1990)}. Animals were sacrificed two months later and examined for tumor development. The result revealed tumor under the kidney capsule, as well as metastases in the peritoneal cavity, causing ascites in all three mice tested. However, no tumor formation was detected following subcutaneous injections.

TRM-1 is Clonal and Undergoes Progressive Karyotypic Changes in Culture

Since multiple foci were initially observed in the originally infected culture, it was important to know whether TRM-1 was derived from one or more infected primary cells. Southern blot analysis with an SV40 T antigen gene probe, was performed on EcoRI-digested TRM-1 DNA isolated at passage 20, revealed only one band. There is only one EcoRI site in TRM-1 (FIG. 8), so the presence of a single band proves that there is only a single retroviral integration site present in TRM-1. Retroviruses integrate randomly in the genome, so a single integration site indicates that TRM-1 is clonal. Because multiple independent foci of cells were present initially in the infected primary culture, it is possible that TRM-1 underwent growth selection in culture, with loss of slower growing clones.

To investigate the possibility that TRM-1 was undergoing changes in vitro, DNA content analysis was performed by flow cytometric analysis on propidium iodide labelled cells. At passage 10, TRM-1 had a diploid DNA content. However, a karyotype analysis performed at passage 25 revealed two populations of cells, both aneuploid, but one with a near diploid karyotype, and one with a near tetraploid karyotype. There were many terminal fusions, with 14p+, Xq+, and 17q+ being the most consistent aberrations.

Oncogene Expression in TRM-1

The expression of the SV-T and H-ras$^{val12}$ rasoncogenes introduced by the retroviral was examined in TRM-1. Immunohistochemical staining demonstrated that SV-T is expressed in TRM-1. H-ras$^{val12}$ expression was analyzed by an ELISA highly specific for ras$^{val12}$ proteins, demonstrating that TRM-1 expresses H-ras$^{val12}$.

Insulin Production from TRM-1

The second important question about TRM-1 is whether it retains the potential to differentiate into a cell that can secrete insulin in response to glucose. It is contemplated that it will be necessary to down-regulate transcription of the oncogenes in TRM-1 in order to achieve efficient differentiation. Preliminary studies was conducted with TRM-1 cells treated with nicotinamide, an agent which has been shown to induce differentiation into insulin-producing cells {Otonkoski, T., et al., J. Clin. Invest., 92:1459–66 (1993)}. Because ICCs respond better to nicotinamide than cells grown in monolayer culture, TRM-1 cells were grown in suspension culture. When grown in this way, they reaggregate to form round structures which greatly resembled ICCs. Cells grown in this way were treated with nicotinamide for varying periods of time and assayed for insulin production using an extremely sensitive radioimmunoassay {Beattie, G., et al., J. Clin. Endocr. Metab., 78:1232–40 (1994)}. The result is shown in Table 2, below ("Nic." in the table denotes nicotinamide).

TABLE 2

INSULIN PRODUCTION FROM TRM-1 CELLS*

| Culture Condition | Day 0 | Day 5 | Day 7 | Day 11 | Day 13 | Day 17 |
|---|---|---|---|---|---|---|
| Monolayer | 0 | 0 | 0 | 0 | 0 | 0 |
| Suspension | 0 | 0 | 0 | 0 | 0 | 0 |
| Suspension + 10 mM Nic. | 0 | 0 | 0 | 2.8 | 4.0 | 5.6 |

*Insulin measurements are expressed as µU insulin/48 hr/ml medium.

Monolayer and suspension cultures of TRM-1 did not produce detectable levels of insulin in the absence of nicotinamide. Suspension cultures in the presence of nicotinamide expressed small amounts of insulin after 11 days of being exposed to nicotinamide. Although the level of insulin production from TRM-1 was low compared to normal ICCs which secrete approximately 100-fold more insulin, there was a clear signal above the background. This result demonstrates that TRM-1 cells have the ability to differentiate into insulin producing cells.

Insulin mRNA was detectable at low levels by RPA. To determine whether low levels of insulin were expressed in all cells or whether TRM-1 cells are heterogeneous in terms of insulin production, insulin immunohistochemistry was performed, showing that most cells were insulin-negative, with rare cells expressing high levels of insulin. Insulin production was not stimulated by treatment with glucose or theophylline, a known insulin secretogogue for fetal β-cells {Milner, R. D. G., et al., J. Endocrinol., 51:323–332 (1971)}. Neither glucagon nor somatostatin mRNA was detectable with RPA, but immunostaining of sections of TRM-1 tumor showed rare glucagon-positive cells.

TRM-1 Does Not Express the β-cell Specific Transcription Factor IPF1/STF-1

Preliminary study suggested that TRM-1 cells do not produce detectable amount of IPF1/STF-1. IPF1/STF-1 is a homeodomain-containing transcription factor that may be important in the control of insulin gene transcription as well as playing a role in pancreatic morphogenesis {Peers, B., et al., Mol. Endocrinol., 8:1798–1806 (1994); Jonsson, J., et al., Nature, 371:606–609 (1994); Ohlsson, H., et al., EMBO J., 12:4251–4259 (1993)}. Western blot analysis using polyclonal rabbit antisera against the amino and carboxyl termini of IPF1/STF-1 showed the absence of IPF1/STF-1 in TRM-1. RPA using the human IPF1/STF-1 cDNA as a probe showed that, although IPF1/STFI MRNA was present in HFP, no IPF1/STF-1 mRNA was detected in TRM-1. If needed, TRM-1 cells may be induced to differentiate, by treating the cells with candidate transcription factors, such as STF-1, or lac repressor. Alternatively, the cells may be treated with farnesyl transferase inhibitors to inhibit ras activity thereby inhibiting cell growth. TRM-1 cells may also be infected with retroviral vectors containing the candidate transcription factor or lac repressor genes to introduce such genes into TRM-1 cells. Other methods known in the art may also be employed. A plasmid with two oncogenes, such as that shown in FIG. 8, can also be used to produce similar cell lines.

In summary, TRM-1 cells were maintained in culture for more than 10 months. In contrast to infected Basinger cells, TRM-1 cells formed tumors under the kidney capsule of nude mice, demonstrating the role of cell type in determining particular properties of transformation. These cell lines retain some differentiated characteristics of endocrine precursor cells, including low levels of hormone production. Suppression of oncogene expression (or oncogene excision) will allow for shut down of oncogene expression and further differentiation. In preliminary experiments in which the lacI gene was introduced into the cells, the cells survived in culture and did not form tumors when injected into nude mice. Suppression of the inducible promoter system in these experiments was incomplete, however (est. at about 90% reduction in oncogene expression) and these cells did not acquire differentiated function as assessed by hormone production. These data suggest that efficient suppression of oncogene expression is important for acquisiton of differentiated function.

EXAMPLE X

Characterization of TRM-6 Cell Line

In the above retroviral infection experiment, five independent cell lines were derived from six independent cultures which grew out within 2–3 weeks after infection. The fact that the cell lines were isolated with relative ease validated the approach of using simultaneous transfer of multiple dominant oncogenes to obtain cell lines from primary human cells and confirmed that the oncogenes that were chosen are able to promote the growth of primary HFP cells. The TRM-1 cell line described supra, while maintaining some properties of endocrine precursor cells, did not have differentiated characteristics of a mature β-cell as is desirable for cell transplantation therapies for treatment of diabetes. In this example, human fetal islets were used as a starting material for cell line creation.

To enrich for insulin-expressing cells, islets from a 24-week human fetal pancreas were selected with 60 mM dithizone. These islets were expanded in vitro (Beattie et al., 1996, Diabetes 45:1223–28) and infected by the retroviral vector, LoTPRRNLo, expressing the SV40 T antigen, H-ras$^{val12}$, and neo genes (Wang et al., 1996, Gene 182:145–150). Foci grew out in separate wells at approximately 10 days postinfection and were expanded in G418 to form individual cell lines, TRM-2 to TRM-6.

Figure 7:
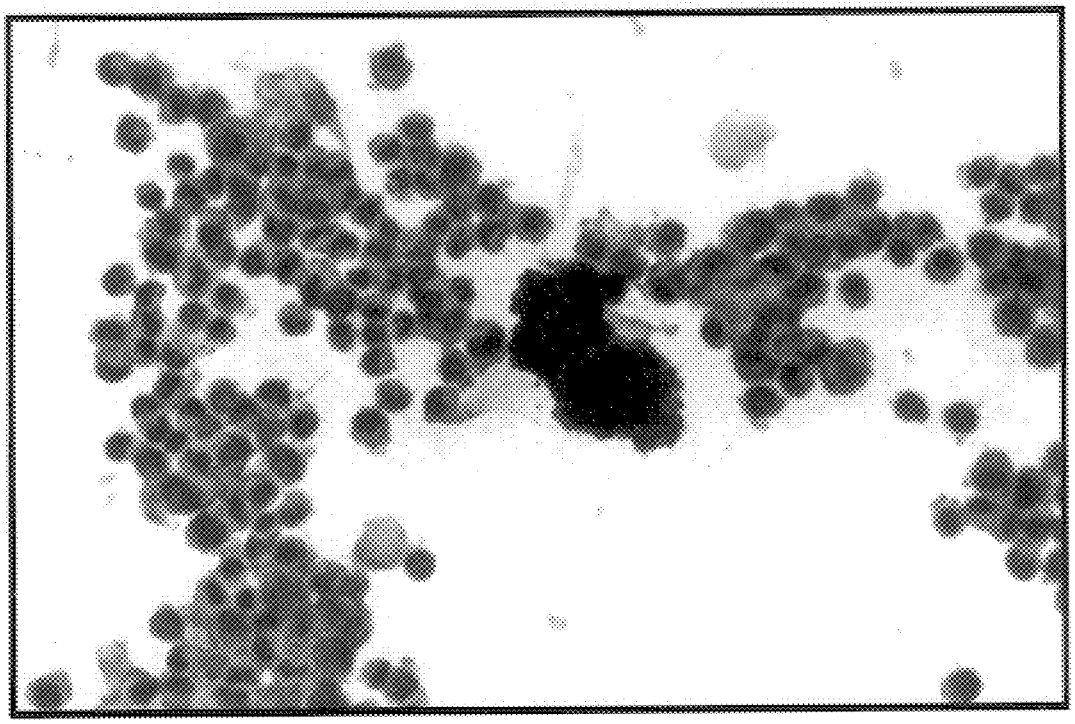
FIG. 7 shows the insulin-positive cells in TRM-6.

The cell lines were screened for insulin content at 4-weeks postinfection. One cell line, TRM-6, secreted detectable but low levels of insulin. TRM-6 cells were subcloned by dilution. In the process some wells were shown to contain high percentage of insulin-positive cells. Insulin expression of TRM-6 cells was analyzed by fixing them in 4% paraformaldehyde and staining them using the immunoalkaline phosphatase technique and guinea pig antiporcine insulin antibodies. Red staining denoted insulin-positive cells. In FIG. 7, a cluster of insulin-positive TRM-6 cells in early passage cultures is shown, surrounded by many insulin-negative cells. Subclones that expressed insulin by immunostaining were isolated at 10-weeks following the establishment of TRM-6. In parallel, a low level of insulin mRNA was detectable using a ribonuclease protection assay, whereas glucagon, somatostatin, and PP were not detectable (data not shown).

Although the insulin-positive cells in TRM-6 were rare (<1%), they were always found in small clusters of two to eight cells (FIG. 7). This suggested that TRM-6 might contain stable subpopulations of cells expressing high levels of insulin. Because the cells had been maintained in G418 selection, these insulin-positive cells must have been infected with the retroviral vector.

Immunostaining for insulin six weeks postinfection revealed clusters of cells with high insulin content and TRM-6 cells maintained insulin expression as detected by immunostaining and ribonuclease protection assay for at least 10 weeks. This longitudinal study of TRM-6 cells suggests that insulin expression probably can continue even after oncogene transformation. However, by 16 weeks, the clones had lost insulin expression, possibly due to deleterious effects of the oncogenes on the differentiation state of the cells and/or a growth disadvantage for insulin-expressing cells. It is predicted that downregulation or suppression of the oncogenes will allow the cells to differentiate and stably express insulin.

Using methods similar to that described above, in further experiments, recombinant retroviruses described in this Example successfully transformed adult pancreatic cells which were grown in the extracellular matrix from 804G cells and HGF/SF in DMEM, supplemented with 10% fetal bovine serum, at 37° C. and 10% $CO_2$. The extracellular matrix from 804G cells and HGF/SF enhanced the infection of the cells, it appears that the matrix and HGF/SF increased mitotic index of the adult cells. The resulting cell lines produced insulin. The cell lines survived in vitro for several cell cycles. After successful infection and transformation, both the adult and fetal pancreatic cell lines appeared not to require matrix from 804G cells and HGF/SF in DMEM for growth.

EXAMPLE XI

Isolation and Characterization of Cell Lines from Human Adult Pancreatic Islets

Twenty-two independent cell lines were isolated from adult human islets by using the same methodology as used for TRM-1 and TRM-6 described above. A number of these cell lines have been screened for insulin, glucagon, and somatostatin. A striking finding of this screening was that all of the cell lines had the same hormone production profile, expressing glucagon and somatostatin. This was confirmed by radioimmunoassay which found 0.12 pmoles/ml/day of glucagon in the media from one line HAP-5 (See Wang et al., 1996, Diabetes 45 supplement 2:285A5.)

EXAMPLE XII

Isolation and Characterization of Cell Lines from Purified Populations of Adult Human β-Cells To guarantee that the cell lines that are produced by infection with retroviral vectors expressing multiple dominant oncogenes are derived from a β-cell as opposed to some other cell present in an adult human islet, fluorescent activated cell sorting was used to isolate a 97% pure populations of human β-cells. From these purified β-cells, a new series of clonal cell lines was derived by infection with LoT-PRRNLo.

β-cells were purified by fluorescence-activated cell sorting using FAD (flavin adenine dinucleotide) autofluorescence and FLS (forward light scatter) as parameters (van de Winkel et al., 1982, Biochem. Biophys. Res. Comm. 107:525–32). This procedure has been successfully to isolate rodent pancreatic β-cells (Cirull et al., 1993, J. Clin. Invest. 91:1868–76; Sekine et al., 1994, J. Biol. Chem. 269:4895–4902; Rouiller et al., 1990, Exp. Cell Res. 191:305–12). These results indicate that this method can also be applied to human β-cells.

Figure 9:
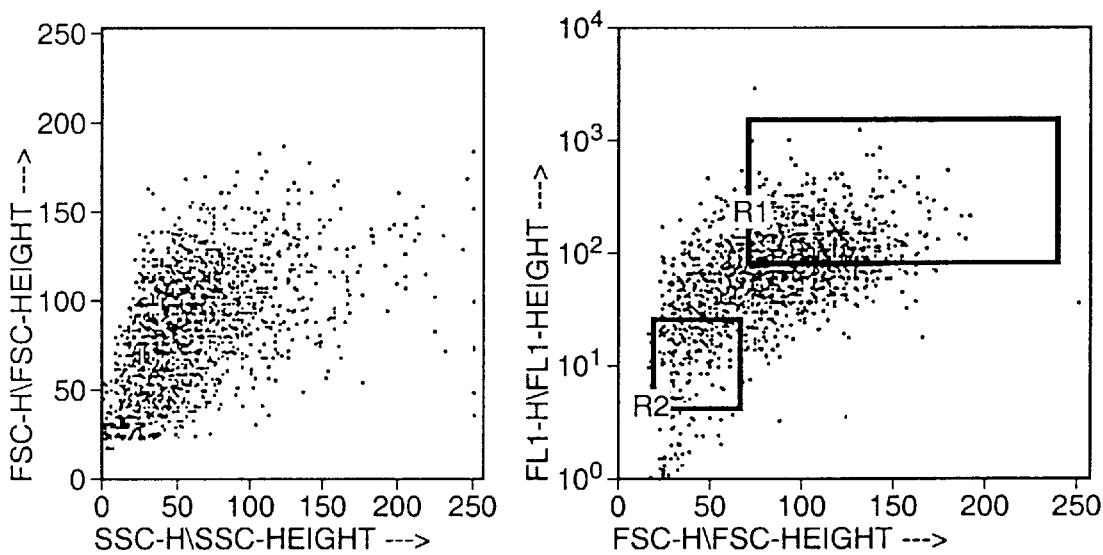
FIG. 9 shows fluoresence-activated cell sorting of cells derived from adult human islets. A single cell suspension of cells derived from whole human pancreatic islets was incubated in 2.8 mM glucose for 15 minutes at 37° C. Islet cell were then analyzed in a FAC$^{Star}$ flow cytometer (Becton Dickinson). Cellular autofluoresecence (FAD) was excited by an argon laser beam tuned to 488 nanometers and plotted (y-axis) against forward light scatter (FLS) (x-axis). The darker area corresponds to the β-cell population which is characterized by higher FAD and FLS. Immunohistochemical analysis of the purified β-cell preparation demonstrated that 98.2% of this cell population was insulin-positive.

A sample of 2,000 human adult islets, was dissociated into a single cell suspension by incubation at 37° C. for 10 minutes in a non-enzymatic cell dissociation medium (Sigma, cat.#C-5789). Gentle pipetting was applied every 15 minutes until all the cells existed as a single cell suspension. The islet cell suspension obtained was then washed in sterile HBSS containing 2% human normal serum and 2.8 mM glucose, and incubated in the same medium for 15 minutes at 37° C. This incubation in low glucose allows β-cells to accumulate the pool of FAD used as an electron carrier in the Krebs cycle. Islet cells were then analyzed in a FAC$^{Star}$ flow cytometer (Becton Dickinson). Cellular autofluorescence (FAD) was excited by an argon laser beam tuned to 488 nm at 500 mW output power, and plotted against forward light scatter (FLS), which relates to cellular size. By this procedure, two cell populations became apparent. (FIG. 9), allowing the separation of β-cells from non-β-cells (α, δ, and PP). Following this procedure, a sample of each sorted population was allowed to adhere to tissue culture-treated slides and assessed for hormone immunoreactivity. The putative β-cell population, separated according to the higher FAD and FLS autofluorescence contained 98.2% insulin-positive cells by immunostaining.

The purified β-cell and non-β-cell subpopulations were placed into culture using extracellular matrix plus HGF/SF (Beattie et al., 1996, Diabetes V45 N9: 1223–28). The cells were expanded using these culture conditions until 5,000–10,000 cells were growing in a well. This is the number that we have typically used for retroviral infection experiments, with the finding of efficient cell line formation. Multiple separate wells were infected for each subpopulation, ensuring that cell lines from different wells result from independent events. The retroviral vector LoTPRRNLo, expressing the SV40 T antigen and H-ras$^{val12}$ oncogenes (Wang et al., 1996, Gene 182:145–150), was added to each well at an approximate multiplicity of infection of ten. Polybrene at a concentration of 4 μg/ml was used to enhance infectivity. One to two weeks following infection, G418 was added to a final concentration of 400 μg/ml to select for infected cells. Previous experience with the LoTPRRNLo retroviral vectors has found that this protocol results in cell line formation with close to 100% efficiency.

Figure 10:
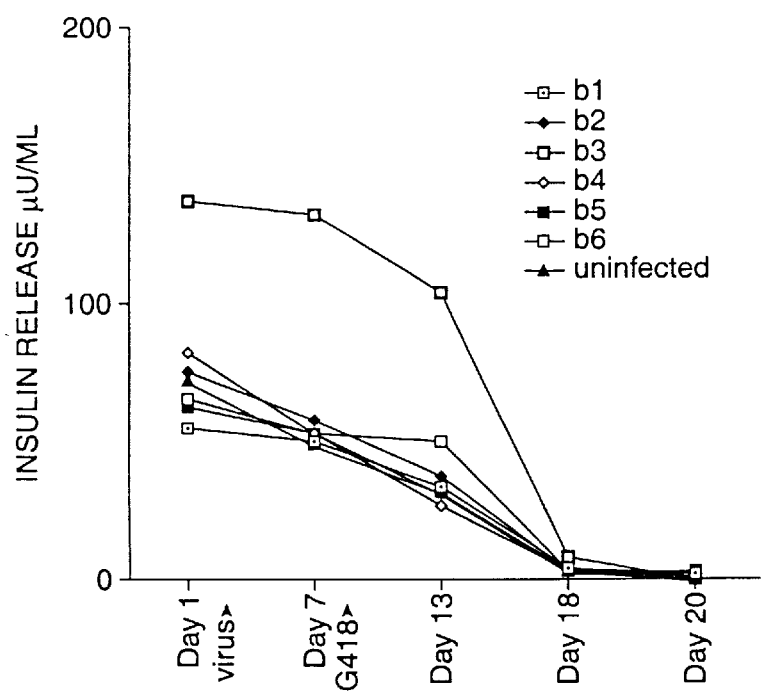
FIG. 10 shows insulin release from β-cell lines.
Figure 11:
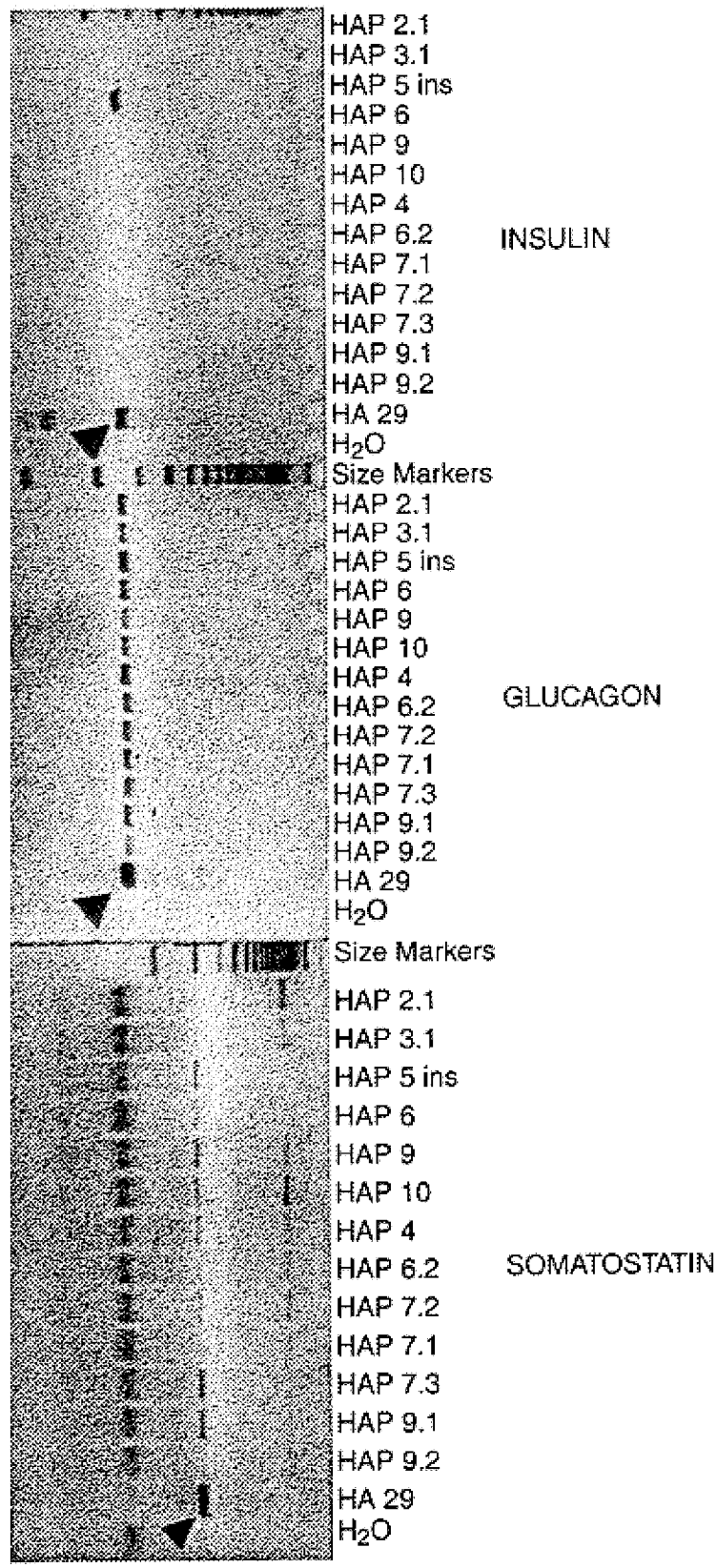
FIG. 11 shows RT-PCR assay for insulin (left panel), glucagon (middle panel) and somatostatin (right panel) in multiple independent cell lines derived from adult human islets (HAP) and primary human islets (HA). Primers for insulin, glucagon and somatostatin spanned introns to distinguish amplification products resulting from contaminating genomic DNA in the RNA samples.

Cell lines that were derived from infection of the purified islet cell populations were maintained in separate wells so that each could be analyzed independently. Each clonal cell line was subjected to analysis for pancreatic hormone expression by RT-PCR using primers specific for insulin, glucagon, somatostatin, and PP and by radioimmunoassay to measure insulin release. Insulin was detected at early times in the culture. Insulin was present following the addition of G418, at a time when all uninfected cells were dead and the medium had been changed to eliminate any residual insulin secreted by uninfected cells (FIG. 10). This indicates that the primary cell from which the cell lines were derived was in fact a β-cell. Interestingly, even though insulin expression was lost from the β-cell lines, glucagon and somatostatin expression could be detected by RT-PCR in all β-cell lines tested (FIG. 11). This indicates that the differentiation state of the β-cell lines has shifted from insulin expression to an earlier phenotype of multiple hormone production. This does not occur with the human fetal pancreatic cell lines TRM-1 and TRM-6, which lose insulin expression but do not show glucagon or somatostatin expression by RPA (see supra and Wang et al., 1997, Cell Transplant. 6:59–67, which is incorporated herein by its entirety) or RT-PCR.

EXAMPLE XIII

Additional Characterization of Cell Lines

Epithelial markers. The cell lines express cytokeratin, EGP40, which is found only in epithelial cells, E-cadherin and N-CAM. The pattern of integrin expression in TRM-1 is qualitatively similar to that of primary HFP epithelial cells, although there are quantitative differences in the levels of individual integrins.

Endocrine precursor markers. β-galactosidase, which we have found to be expressed at high levels in HFP endocrine precursors, is present at high levels in TRM-1 and TRM-6. Tyrosine hydroxylase, which is expressed in at least some β-cell precursors and is limited to a subset of the epithelial cells expressing high levels of β-galactosidase, is not expressed in TRM-1 when examined by immunohistochemistry or RNase protection assay.

Glucose transport and sensing molecules. TRM-1, TRM-6, and HAP-5 cells have been examined for the expression of both GLUT2 and glucokinase using RT-PCR. GLUT2, which in the mouse is a marker for β-cell precursors, was detected in TRM-1, TRM-6, and HAP-5. Glucokinase was detected in primary tissue but not in the cell lines.

Islet cell antigens. TRM-1 and TRM-6 cells express ICA69 analyzed by RPA, but do not express glutamic acid decarboxylase.

PDX-1 expression. PDX-1 expression is not detected in TRM-1, TRM-6, or HAP-5 by RT-PCR, Western blot analysis using polyclonal rabbit antisera against the amino and carboxyl termini of PDX-1 or by RPA using the human PDX-1 cDNA as a probe. When PDX-1 is expressed in TRM-6 using a retroviral vector, there is an increase in the level of somatostatin mRNA, but insulin expression is not induced.

Deposit

The following TRM-1 and TRM-6 cell lines, and pLNS-VoTPMPRL and pLoTPMPRRRNLo vectors, have been deposited under the Budapest Treaty, at the American Type Culture Collection, Rockville, Md. 20852, USA, with the following ATCC Accession numbers:

| Designation | Deposit Date | ATCC No. |
|---|---|---|
| TRM-1 | Jan. 26, 1995 | CRL 11827 |
| TRM-6 | Jan. 26, 1995 | CRL 11828 |
| pLNSVoTPMPRL | Jan. 26, 1995 | 97038 |
| pLoTPMPRRNLo | Jan. 26, 1995 | 97037 |

Availability of the deposited cell lines and vectors is not to be construed as a license to practice the invention in contravention of the rights granted under the authority of any government in accordance with its patent laws.

Also, the present invention is not to be considered limited in scope by the deposited recombinant vectors and cell lines, since the deposited vectors and cell lines are intended only to be illustrative of particular aspects of the invention. Any recombinant vector which can be used to prepare recombinant microorganism which can function to produce the cell lines described in this application is considered to be within the scope of this invention. Further, various modifications of the invention in addition to those shown and described herein which are apparent to those skilled in the art from the preceding description are considered to fall within the scope of the appended claims.

We claim:

1. A vector comprising at least two oncogenes and a pair of genetic elements flanking the oncogenes, wherein the genetic elements comprise recombination sites, and wherein said vector further comprises an additional gene.

2. The vector of claim 1, wherein the vector comprises two or three oncogenes.

3. The vector of claim 1, further comprising one or more inducible promoters, wherein the expression of each oncogene is under the transcriptional control of an inducible promoter.

4. A cell transfected by the vector of claim 1.

5. The vector of claim 2 wherein the vector is a retroviral vector.

6. The vector of claim 3, wherein the vector is a recombinant virus encoding two or three oncogenes and at least one inducible promoter.

7. Progeny of the cell of claim 4.

8. The cell of claim 4, wherein the cell is a human cell.

9. The retroviral vector of claim 5, wherein the oncogenes are Ras and SV40 T-Ag.

10. A vector comprising a first gene that is an oncogene and a second gene that encodes a downstream effector of ras, said vector further comprising a pair of genetic elements flanking the first and second genes, wherein the genetic elements comprise recombination sites.

11. A mammalian cell comprising recombination sites not naturally found in the cell, wherein at least two oncogenes lie between said recombination sites.

12. A method for producing a non-naturally occurring cell comprising transforming a cell with a retroviral vector comprising at least two oncogenes flanked by recombination sites, allowing the transformed cell to divide at least once, and introducing recombinase into the cell, whereupon said at least two oncogenes are excised, thereby producing a non-naturally occurring cell.

13. The method of claim 12 wherein the cell is from pancreas.

14. The method of claim 12 wherein:

(i) the recombination sites are from bacteriophage PI and the recombinase is Cre recombinase; or (ii) the recombination sites are FLP target sites and the recombinase is FLP.

15. A cell produced by the method of claim 12.

16. The method of claim 13, wherein the cell produces insulin after excision of the oncogenes.

17. The method of claim 14 wherein the recombinase is encoded by a gene under the transcriptional control of an inducible promoter and the step of introducing the recombinase into the cell comprises inducing transcription of the gene.

18. A cell produced by the method of claim 14.

19. A pancreatic cell comprising two or more exogenous oncogenes flanked by recombination sites not naturally found in the cell.

20. The pancreatic cell of claim 19, comprising two or three oncogenes.

21. Progeny of the cell of claim 19.

22. A cell of claim 20, wherein said cell is of human origin and wherein said cell comprises ras and SV40 T-Ag.

23. A method for producing a non-naturally occurring cell comprising transforming a cell with a retroviral vector comprising two or more exogenous oncogenes flanked by recombination sites from bacteriophage PI, allowing the transformed cell to divide at least once, and introducing Cre recombinase into the cell whereupon the oncogenes are excised.

24. A non-naturally occurring human pancreatic cell line comprising at least two exogenous oncogenes, wherein said cell line is capable of surviving in vitro for at least 50 cell divisions or six months when grown in Dulbecco's Modified Eagle Medium (DMEM) with 10% fetal bovine serum at 37° C. and 10% $CO_2$ or the progeny of said cell line.

25. The non-naturally occurring human pancreatic cell line of claim 24, wherein the cell line produces insulin.

26. The non-naturally occurring human pancreatic cell line of claim 24, wherein cells of the cell line contain at least two exogenous oncogenes under the control of an inducible promoter.

27. The non-naturally occurring human pancreatic cell line of claim 26, wherein cells of the cell line contain two to five exogenous oncogenes under the transcriptional control of an inducible promoter.

* * * * *